(12) United States Patent
Snell et al.

(10) Patent No.: US 10,662,128 B2
(45) Date of Patent: May 26, 2020

(54) AROMATIZATION PROCESSES USING BOTH FRESH AND REGENERATED CATALYSTS, AND RELATED MULTI-REACTOR SYSTEMS

(71) Applicant: Chevron Phillips Chemical Company LP, The Woodlands, TX (US)

(72) Inventors: Ryan W. Snell, Kingwood, TX (US); Gabriela D. Alvez-Manoli, Kingwood, TX (US); Xianghong Hao, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/896,127

(22) Filed: Feb. 14, 2018

(65) Prior Publication Data

US 2019/0249091 A1    Aug. 15, 2019

(51) Int. Cl.

| | | |
|---|---|---|
| *C07C 5/41* | (2006.01) | |
| *B01J 29/62* | (2006.01) | |
| *B01J 35/00* | (2006.01) | |
| *B01J 35/10* | (2006.01) | |
| *B01J 38/48* | (2006.01) | |
| *B01J 38/42* | (2006.01) | |
| *C10G 35/085* | (2006.01) | |
| *C10G 35/095* | (2006.01) | |

(Continued)

(52) U.S. Cl.

CPC ............... *C07C 5/417* (2013.01); *B01J 23/42* (2013.01); *B01J 29/068* (2013.01); *B01J 29/62* (2013.01); *B01J 29/90* (2013.01); *B01J 35/0006* (2013.01); *B01J 35/0073* (2013.01); *B01J 35/108* (2013.01); *B01J 35/1014* (2013.01); *B01J 35/1019* (2013.01); *B01J 35/1038* (2013.01); *B01J 38/42* (2013.01); *B01J 38/48* (2013.01); *C07C 5/393* (2013.01); *C10G 35/085* (2013.01); *C10G 35/095* (2013.01); *B01J 2231/52* (2013.01); *C07C 2529/62* (2013.01); *C10G 2400/30* (2013.01)

(58) Field of Classification Search
None
See application file for complete search history.

(56) References Cited

U.S. PATENT DOCUMENTS

| 2,969,318 A | 1/1961 | Woodall |
| 3,249,405 A | 5/1966 | Waddill |

(Continued)

FOREIGN PATENT DOCUMENTS

| WO | 2013062695 | 5/2013 |
| WO | 2013134055 | 9/2013 |

OTHER PUBLICATIONS

Saint-Gobain NorPro "MacroTrap® XPore 80 Guard Bed Media," 2011, 2 pages.

(Continued)

*Primary Examiner* — In Suk C Bullock
*Assistant Examiner* — Alyssa L Cepluch
(74) *Attorney, Agent, or Firm* — Merchant & Gould P.C.

(57) ABSTRACT

Multi-reactor systems with aromatization reactor vessels containing a catalyst with low surface area and pore volume, followed in series by aromatization reactor vessels containing a catalyst with high surface area and pore volume, are disclosed. Related reforming methods using the different aromatization catalysts also are described.

17 Claims, 10 Drawing Sheets

(51) Int. Cl.
  *B01J 23/42*    (2006.01)
  *B01J 29/068*   (2006.01)
  *B01J 29/90*    (2006.01)
  *C07C 5/393*    (2006.01)

(56) References Cited

U.S. PATENT DOCUMENTS

| | | | |
|---|---|---|---|
| 4,456,527 A | 6/1984 | Buss et al. | |
| 4,741,819 A | 5/1988 | Robinson et al. | |
| 4,937,215 A | 6/1990 | Murakawa et al. | |
| 4,940,532 A | 7/1990 | Peer et al. | |
| 5,059,304 A | 10/1991 | Field | |
| 5,155,075 A * | 10/1992 | Innes | B01J 29/90 208/138 |
| 5,196,631 A | 3/1993 | Murakawa et al. | |
| 5,260,238 A | 11/1993 | Murakawa et al. | |
| 5,316,992 A | 5/1994 | Russ et al. | |
| 5,322,615 A | 6/1994 | Holtermann et al. | |
| 5,389,235 A | 2/1995 | Russ et al. | |
| 5,401,365 A | 3/1995 | Chen et al. | |
| 5,401,386 A | 3/1995 | Morrison et al. | |
| 5,507,939 A | 4/1996 | Russ et al. | |
| 5,518,607 A | 5/1996 | Field et al. | |
| 5,520,798 A | 5/1996 | Innes | |
| 5,585,075 A | 12/1996 | Takano et al. | |
| 5,601,698 A | 2/1997 | Innes | |
| 5,611,914 A | 3/1997 | Prince et al. | |
| 5,614,082 A | 3/1997 | Russ et al. | |
| 5,866,743 A | 2/1999 | Heyse et al. | |
| 6,190,539 B1 * | 2/2001 | Holtermann | B01J 29/064 208/135 |
| 6,207,042 B1 | 3/2001 | Holtermann et al. | |
| 6,406,614 B1 | 6/2002 | Tiedtke et al. | |
| 6,518,470 B1 | 2/2003 | Fukunaga et al. | |
| 6,548,030 B2 | 4/2003 | Heyse et al. | |
| 6,812,180 B2 | 11/2004 | Fukunaga | |
| 7,153,801 B2 | 12/2006 | Wu | |
| 7,544,335 B2 | 6/2009 | Scanlen et al. | |
| 7,582,272 B2 | 9/2009 | Glova et al. | |
| 7,687,673 B2 | 3/2010 | Ablin | |
| 7,932,425 B2 | 4/2011 | Blessing et al. | |
| 8,119,203 B2 | 2/2012 | Hise et al. | |
| 8,664,144 B2 | 3/2014 | Wu | |
| 8,716,161 B2 | 5/2014 | Wu | |
| 8,912,108 B2 | 12/2014 | Wu | |
| 9,085,736 B2 * | 7/2015 | Morrison | C10G 35/04 |
| 9,387,467 B2 | 7/2016 | Khare | |
| 2002/0065443 A1 | 5/2002 | Williams et al. | |
| 2004/0192862 A1 | 9/2004 | Glover | |
| 2013/0109897 A1 | 5/2013 | Morrison et al. | |

OTHER PUBLICATIONS

International Search Report & Written Opinion PCT/US2019/018089, dated May 9, 2019, 11 pages.

* cited by examiner

AROMATIZATION PROCESSES USING BOTH FRESH AND REGENERATED CATALYSTS, AND RELATED MULTI-REACTOR SYSTEMS

FIELD OF THE INVENTION

The present disclosure concerns catalytic reforming methods and related aromatization reactor vessels, and more particularly relates to the use of a fresh aromatization catalyst and a regenerated aromatization catalyst in different reactor vessels within a multi-reactor system.

BACKGROUND OF THE INVENTION

The catalytic conversion of non-aromatic hydrocarbons into aromatic compounds, often referred to as aromatization or reforming, is an important industrial process that can be used to produce benzene, toluene, xylenes, and the like. The aromatization or reforming process often is conducted in a reactor system that can contain two or more reactors containing transition metal based catalysts. These catalysts can provide increased selectivity to the desired aromatic compounds. However, under commercial reaction conditions, these catalysts slowly lose their activity, often simultaneously with a loss of selectivity to the desired aromatic compounds. Such catalysts are often referred to as "spent" catalysts once economic or operational thresholds are passed, and such spent catalysts can be "regenerated" using various procedures and techniques.

Due to the raw material cost of fresh catalyst, it would be beneficial to use regenerated catalyst in combination with fresh catalyst in aromatization reactor systems and related aromatization processes. Accordingly, it is to these ends that the present disclosure is generally directed.

SUMMARY OF THE INVENTION

Various aromatization processes are disclosed and described herein. One such aromatization process can comprise (i) introducing a first hydrocarbon feed into at least one first reactor vessel comprising a first aromatization catalyst, and contacting the first hydrocarbon feed with the first aromatization catalyst under first reforming conditions to produce a first aromatic product; wherein the first aromatization catalyst (e.g., a regenerated aromatization catalyst) comprises a first transition metal and a first catalyst support, the first aromatization catalyst characterized by a first surface area in a range from about 80 $m^2/g$ to about 150 $m^2/g$, and/or a first micropore volume in a range from about 0.01 cc/g to about 0.048 cc/g; (ii) discharging a first effluent comprising the first aromatic product from the at least one first reactor vessel; (iii) heating the first effluent to form a second hydrocarbon feed; (iv) introducing the second hydrocarbon feed into at least one second reactor vessel comprising a second aromatization catalyst, and contacting the second hydrocarbon feed with the second aromatization catalyst under second reforming conditions to produce a second aromatic product; wherein the second aromatization catalyst (e.g., a fresh aromatization catalyst) comprises a second transition metal and a second catalyst support, the second aromatization catalyst characterized by a second surface area in a range from about 160 $m^2/g$ to about 260 $m^2/g$, and/or a second micropore volume in a range from about 0.05 cc/g to about 0.09 cc/g; and (v) discharging a second effluent comprising the second aromatic product from the at least one second reactor vessel.

Also disclosed herein are aromatization reactor vessel systems. For example, an illustrative aromatization reactor vessel system can comprise (A) at least one first reactor vessel comprising (a1) a first reactor inlet for introducing a first hydrocarbon feed into the at least one first reactor vessel; (a2) a first aromatization catalyst for catalytically converting at least a portion of the first hydrocarbon feed under first reforming conditions to produce a first aromatic product; wherein the first aromatization catalyst (e.g., a regenerated aromatization catalyst) comprises a first transition metal and a first catalyst support; the first aromatization catalyst characterized by a first surface area in a range from about 80 $m^2/g$ to about 150 $m^2/g$, and/or a first micropore volume in a range from about 0.01 cc/g to about 0.048 cc/g; and (a3) a first reactor outlet for discharging a first effluent comprising the first aromatic product from the at least one first reactor vessel; (B) at least one second reactor vessel comprising (b1) a second reactor inlet for introducing a second hydrocarbon feed into the at least one second reactor vessel; (b2) a second aromatization catalyst for catalytically converting at least a portion of the second hydrocarbon feed under second reforming conditions to produce a second aromatic product; wherein the second aromatization catalyst (e.g., a fresh aromatization catalyst) comprises a second transition metal and a second catalyst support, the second aromatization catalyst characterized by a second surface area in a range from about 160 $m^2/g$ to about 260 $m^2/g$, and/or a second micropore volume in a range from about 0.05 cc/g to about 0.09 cc/g; and (b3) a second reactor outlet for discharging a second effluent comprising the second aromatic product from the at least one second reactor vessel; and (C) a furnace positioned between the first reactor outlet and the second reactor inlet, the furnace capable of heating the first effluent to form the second hydrocarbon feed.

In these and other aspects of the invention, the at least one first reactor vessel can comprise one first reactor vessel or a series of two or more first reactor vessels. Likewise, the at least one second reactor vessel can comprise one second reactor vessel or a series of two or more second reactor vessels.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE DRAWINGS

The accompanying drawings, which are incorporated in and constitute a part of this disclosure, illustrate various aspects of the present invention. In the drawings.

DEFINITIONS

Figure 1:
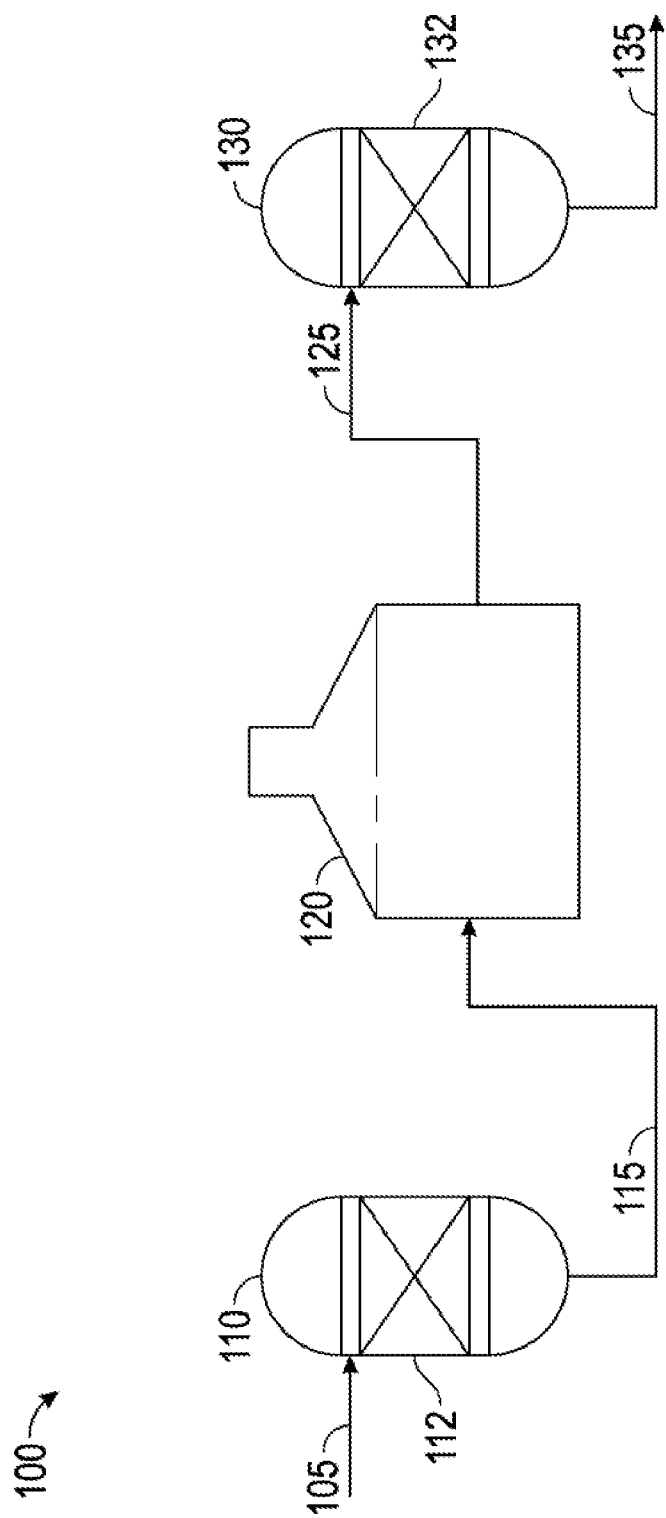
FIG. 1 illustrates a reactor system containing two reactor vessels and a furnace, in an aspect of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein can be combined to describe inventive designs, compositions, processes, or methods consistent with the present disclosure.

While apparatuses, systems, and methods/processes are described herein in terms of "comprising" various components, devices, or steps, the apparatuses, systems, and methods/processes can also "consist essentially of" or "consist of" the various components, devices, or steps, unless stated otherwise.

The terms "a," "an," and "the" are intended to include plural alternatives, e.g., at least one. For instance, the disclosure of "a transition metal" or "a furnace," is meant to encompass one, or mixtures or combinations of more than one, transition metal or furnace, unless otherwise specified.

A "spent" catalyst is used herein generally to describe a catalyst that has unacceptable performance in one or more of catalyst activity, selectivity to a desired product(s), or an operating parameter, such as maximum operating temperature or pressure drop across a reactor, although the determination that a catalyst is "spent" is not limited only to these features. The unacceptable performance of the spent catalyst can be due to a sulfur or carbonaceous build-up on the catalyst over time, but is not limited thereto. In some aspects, the "fresh" catalyst can have an activity X, the "spent" catalyst can have an activity Z, and a "regenerated" catalyst can have an activity Y, such that $Z<Y\leq X$. In certain aspects disclosed herein, the regenerated catalyst can have substantially the same catalyst activity as that of the fresh catalyst. Such catalyst activity comparisons (and other reforming performance characteristics, such as selectivity) are meant to use the same production run (batch) of catalyst, tested on the same equipment, and under the same test method and conditions. The "regenerated" catalyst encompasses catalysts that are regenerated using any suitable combination of catalyst regeneration steps, and optionally, this can include a reduction step (e.g., using hydrogen).

The amounts of any components or materials present on the catalysts described herein are on a weight basis, such as wt. % or ppmw (ppm by weight), unless otherwise specified. These components or materials can include, for instance, the amount of carbon, the amount of fluorine, the amount of chlorine, the amount of platinum, and so forth.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, noble metals for Group 8-10 elements, and halogens or halides for Group 17 elements.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes a n-butyl group, a sec-butyl group, an iso-butyl group, and a t-butyl group.

In one aspect, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. As a representative example, the present application discloses that the methods provided herein can employ a catalyst containing F and Cl at a molar ratio of F:Cl in a range from about 0.5:1 to about 4:1 in certain aspects. By a disclosure that the molar ratio of F:Cl can be in a range from about 0.5:1 to about 4:1, the intent is to recite that the molar ratio can be any molar ratio within the range and, for example, can be equal to about 0.5:1, about 0.6:1, about 0.7:1, about 0.8:1, about 0.9:1, about 1:1, about 2:1, about 3:1, or about 4:1. Additionally, the molar ratio of F:Cl can be within any range from about 0.5:1 to about 4:1 (for example, the molar ratio can be in a range from about 0.5:1 to about 2:1), and this also includes any combination of ranges between about 0.5:1 and about 4:1. Likewise, all other ranges disclosed herein should be interpreted in a manner similar to this example.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The term "substituted" when used to describe a group, for example, when referring to a substituted analog of a particular group, is intended to describe any non-hydrogen moiety that formally replaces a hydrogen atom in that group, and is intended to be non-limiting. A group or groups can also be referred to herein as "unsubstituted" or by equivalent terms such as "non-substituted," which refers to the original group in which a non-hydrogen moiety does not replace a hydrogen atom within that group. Unless otherwise specified, "substituted" is intended to be non-limiting and include inorganic substituents or organic substituents as understood by one of ordinary skill in the art.

As used herein, the terms "hydrocarbon" or "hydrocarbon feed" refer to compounds containing only carbon and hydrogen atoms. Other identifiers can be utilized to indicate the presence of particular groups, if any, in the hydrocarbon (e.g., halogenated hydrocarbon indicates that the presence of one or more halogen atoms replacing an equivalent number of hydrogen atoms in the hydrocarbon). The hydrocarbon or hydrocarbon feed may be a naphtha stream or light naphtha stream. In certain aspects, the hydrocarbon feed may comprise $C_6$-$C_8$ alkanes and/or cycloalkanes (e.g., hexane, heptane, cyclohexane, and methylcyclohexane, among others). In the cases where the catalyst may be a sulfur-sensitive catalyst, such as a large-pore zeolite catalyst comprising at least one alkali or alkaline earth metal and at least one Group VIII metal, the hydrocarbon or hydrocarbon feed may be a low-sulfur hydrocarbon or a low-sulfur naphtha stream and may contain less than about 100 parts per billion by weight (ppb) sulfur; alternatively, less than about 50 ppb sulfur; or alternatively, less than about 25 ppb sulfur.

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (aromatic hydrocarbon compounds, e.g., benzene, toluene, and xylenes) and "heteroarenes" (heteroaromatic compounds formally derived from arenes by replacement of one or more methine (—C═) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" can be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers can be utilized to indicate the presence of particular groups, if any, in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group can be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers can be utilized to indicate the presence of particular groups, if any, in the cycloalkane (e.g., halogenated cycloalkane indicates that the presence of one or more halogen atoms replacing an equivalent number of hydrogen atoms in the cycloalkane).

The term "halogen" has its usual meaning. Examples of halogens include fluorine, chlorine, bromine, and iodine.

The term "contacting" is used herein to describe methods, processes, and compositions wherein the components are contacted or combined together in any order, in any manner, and for any length of time, unless otherwise specified. For example, the components can be contacted by blending or mixing. Further, unless otherwise specified, the contacting of any component can occur in the presence or absence of any other component of the methods, processes, and compositions described herein. Combining additional materials or components can be done by any suitable technique. Further, "contacting" two or more components can result in a solution, a slurry, a mixture, a reaction mixture, or a reaction product.

Molar selectivities to a desired product are defined as:

Benzene selectivity: $\qquad$ Eq. 1

$$S_{Bz} = \frac{\dot{n}_{Bz,prod}}{\dot{n}_{convC6,feed} - \dot{n}_{conv\,C6,prod}}$$

Toluene selectivity: $\qquad$ Eq. 2

$$S_{Tol} = \frac{\dot{n}_{Tol,prod}}{\dot{n}_{convC7,feed} - \dot{n}_{conv\,C7,prod}}$$

Benzene + Toluene selectivity: $\qquad$ Eq. 3

$$S_{Bz}+_{Tol} = \frac{\dot{n}_{Bz,prod} + \dot{n}_{Tol,prod}}{\dot{n}_{convC6,C7,feed} - \dot{n}_{conv\,C6,C7,prod}}$$

Aromatics selectivity: $\qquad$ Eq. 4

$$S_{arom} = \frac{\dot{n}_{Bz,prod} + \dot{n}_{Tol,prod} + \dot{n}_{C8+arom,prod}}{\dot{n}_{convC6-C8+,feed} - \dot{n}_{conv\,C6-C8+,prod}}$$

Conversion is defined as the number of moles converted per mol of "convertible" hydrocarbons fed:

C6 conversion  Eq. 5

$$X_{C6} = \frac{\dot{n}_{convC6,feed} - \dot{n}_{convC6,prod}}{\dot{n}_{convC6,feed}}$$

C7 conversion  Eq. 6

$$X_{C7} = \frac{\dot{n}_{convC7,feed} - \dot{n}_{convC7,prod}}{\dot{n}_{convC7,feed}}$$

C6 + C7 conversion  Eq. 7

$$X_{C6+C7} = \frac{\dot{n}_{convC6,feed} + \dot{n}_{convC7,feed} - \dot{n}_{convC6,prod} - \dot{n}_{convC7,prod}}{\dot{n}_{convC6,feed} + \dot{n}_{convC7,feed}}$$

In these equations, n indicates a molar flow rate in a continuous reactor or the number of moles in a batch reactor.

As used herein, the term "convertible hydrocarbon," "convertible $C_6$ species," or "convertible $C_7$ species" refers to a hydrocarbon compound that is readily reacted to form aromatic hydrocarbons under aromatization process conditions. A "non-convertible hydrocarbon" is a highly-branched hydrocarbon that is not readily reacted to form aromatic hydrocarbons under aromatization process conditions. A "non-convertible hydrocarbon" can comprise highly-branched hydrocarbons having six or seven carbon atoms with an internal quaternary carbon, or hydrocarbons having six carbons atoms and two adjacent internal tertiary carbons, or mixtures thereof. A "convertible $C_6$ species" is a hydrocarbon containing six carbons without an internal quaternary carbon or two adjacent internal tertiary carbons, for example, n-hexane, 2-methyl-pentane, 3-methyl-pentane, cyclohexane, and methyl cyclopentane. A "convertible $C_7$ species" is a hydrocarbon containing seven carbons without an internal quaternary carbon, for example, n-heptane, 2-methyl-hexane, 3-methyl-hexane, 2,3-dimethyl-pentane, 2,4-dimethyl-pentane, methyl cyclohexane, and dimethyl cyclopentane. The highly branched hydrocarbons with six or seven carbon atoms and an internal quaternary carbon can comprise, for example, 2,2-dimethylbutane, 2,2-dimethyl-pentane, 3,3-dimethylpentane, and 2,2,3-trimethylbutane. The highly branched hydrocarbons with six carbon atoms and an adjacent internal tertiary carbon can comprise, for example, 2,3-dimethylbutane. The non-convertible highly branched hydrocarbons do not easily convert to aromatic products, and instead tend to convert to light hydrocarbons under aromatization process conditions.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The following detailed description refers to the accompanying drawings. Wherever possible, the same or similar reference numbers are used in the drawings and the following description to refer to the same or similar elements or features. While various aspects of the invention are described, modifications, adaptations, and other implementations are possible. For example, substitutions, additions, or modifications can be made to the elements illustrated in the drawings, and the methods described herein can be modified by substituting, reordering, or adding stages to the disclosed methods. Accordingly, the following detailed description and its exemplary aspects do not limit the scope of the invention.

Beneficially, the aromatization reactor vessel systems and processes disclosed herein can employ a first aromatization catalyst that has lower surface area, lower pore volume, and lower platinum dispersion than the second aromatization catalyst. Further, the first aromatization catalyst also can contain higher levels of iron, sulfur, and carbon than the second aromatization catalyst. Yet, despite these perceived negative catalyst attributes, and unexpectedly, it was found that the first aromatization catalyst (which can be a regenerated catalyst) often has catalyst selectivity that is equivalent or even superior to that of the second aromatization catalyst (which can be a fresh catalyst). Typically, the first aromatization catalyst (e.g., a regenerated catalyst) has lower catalyst activity than the second aromatization catalyst (e.g., a fresh catalyst).

Thus, aromatization reactor vessel systems and processes can be designed as described herein, in which regenerated catalysts can be used, instead of fresh catalysts (and the associated raw material costs), in the early stages of aromatization systems and processes to convert the relatively more easily convertible hydrocarbons (e.g., cyclohexane) with excellent selectivity, and where the lower catalyst activity is not detrimental to the overall system and process.

Aromatization Reactor Vessel Systems

Generally, aromatization reactor vessel systems consistent with the present invention can comprise (A) at least one first reactor vessel comprising (a1) a first reactor inlet for introducing a first hydrocarbon feed into the at least one first reactor vessel; (a2) a first aromatization catalyst for catalytically converting at least a portion of the first hydrocarbon feed under first reforming conditions to produce a first aromatic product; wherein the first aromatization catalyst (e.g., a regenerated aromatization catalyst) comprises a first transition metal and a first catalyst support; the first aromatization catalyst characterized by a first surface area in a range from about 80 m$^2$/g to about 150 m$^2$/g, and/or a first micropore volume in a range from about 0.01 cc/g to about 0.048 cc/g; and (a3) a first reactor outlet for discharging a first effluent comprising the first aromatic product from the at least one first reactor vessel; (B) at least one second reactor vessel comprising (b1) a second reactor inlet for introducing a second hydrocarbon feed into the at least one second reactor vessel; (b2) a second aromatization catalyst for catalytically converting at least a portion of the second hydrocarbon feed under second reforming conditions to produce a second aromatic product; wherein the second aromatization catalyst (e.g., a fresh aromatization catalyst) comprises a second transition metal and a second catalyst support, the second aromatization catalyst characterized by a second surface area in a range from about 160 m$^2$/g to about 260 m$^2$/g, and/or a second micropore volume in a range from about 0.05 cc/g to about 0.09 cc/g; and (b3) a second reactor outlet for discharging a second effluent comprising the second aromatic product from the at least one second reactor vessel; and (C) a furnace positioned between the first reactor outlet and the second reactor inlet, the furnace capable of heating the first effluent to form the second hydrocarbon feed.

FIG. 1 illustrates an aromatization reactor vessel system 100 consistent with the present invention. While not being limited thereto, the aromatization reactor vessel system 100 is described herein as it pertains to its use in the catalytic conversion of a non-aromatic hydrocarbon to produce an aromatic hydrocarbon, examples of which include benzene, toluene, or xylenes, as well as mixtures thereof. The aromatization reactor vessel system 100 in FIG. 1 contains a first reactor vessel 110, a second reactor vessel 130, and a furnace 120 positioned between the reactor vessels. The first reactor vessel 110 includes a first reactor inlet 105 for introducing a first hydrocarbon feed into the first reactor vessel 110, a first reactor outlet 115 for discharging a first effluent that contains a first aromatic product, and a first aromatization catalyst 112, positioned in the first reactor vessel 110, for catalytically converting at least a portion of the first hydrocarbon feed to produce the first aromatic product.

Likewise, the second reactor vessel 130 includes a second reactor inlet 125 for introducing a second hydrocarbon feed into the second reactor vessel 130, a second reactor outlet 135 for discharging a second effluent that contains a second aromatic product, and a second aromatization catalyst 132, positioned in the second reactor vessel 130, for catalytically converting at least a portion of the second hydrocarbon feed to produce the second aromatic product. As described herein, both the first reactor vessel 110 and the second reactor vessel 130 generally are configured for a catalytic conversion of non-aromatic hydrocarbons to aromatic hydrocarbons, such as benzene and toluene.

The furnace 120 is positioned between the reactor vessels as shown in FIG. 1, specifically, between the first reactor outlet 115 and the second reactor inlet 125. The furnace 120 in FIG. 1 is capable of heating the first effluent (in the first reactor outlet 115 from the first reactor vessel 110) to form the second hydrocarbon feed (in the second reactor inlet 125 to the second reactor vessel 130). Generally, the furnace 120 is configured to heat the first effluent to a reforming temperature that is employed in the second reactor vessel 130, often ranging from about 350° C. to about 600° C. While not shown in FIG. 1, a furnace can precede the first reactor vessel 110, and can heat the first hydrocarbon feed in the first reactor inlet 105 to the desired reforming temperature of the first reactor vessel 110, also often in a range from about 350° C. to about 600° C.

The first reactor vessel 110, the furnace 120, and the second reactor vessel 130 can be constructed of any suitable metal material, the selection of which can depend upon the desired operating temperature, desired operating pressure, and inertness to the reactor contents (for example, catalyst, $H_2$, aromatic hydrocarbons, non-aromatic hydrocarbons), amongst other factors. Typical metal materials include austenitic stainless steels, including 304, 316, 321, 347, 410S, 600, or 800 stainless steel, and the like. Moreover, a protective coating or layer containing any suitable material, compound, alloy, or metal, such as tin, can used on any surface in the first reactor vessel 110, the furnace 120, and/or the second reactor vessel 130 to provide resistance to carburization and metal dusting. The metal protective layer may comprise a nickel-depleted bonding layer disposed between the metal materials and the metal protective layer, wherein the metal protective layer is formed by applying a layer of at least one metal to the metal materials to form an applied metal layer on the substrate and curing the applied metal layer form the metal protective layer on the substrate. The metal protective layer optionally may be further processed by mobilization and sequestration processes. The applied metal layer may comprise tin oxide, a decomposable tin compound, and tin metal powder. The applied metal layer may be cured at a temperature of from about 1,220° F. (660° C.) to about 1,400° F. (760° C.) and/or at a pressure of from about 315 psia (2,172 kPa) to about 1 psia (0.05 Pa). The bonding layer may comprise stannide and may have a thickness of about 1 to about 100 μm. The bonding layer may comprise from about 1 wt. % to about 20 wt. % elemental tin. The coated metal materials may be an any metal materials that contact a low-sulfur hydrocarbon. Representative protective layer materials are disclosed in U.S. Pat. Nos. 5,866,743, 6,548,030, 8,119,203, and 9,085,736, which are incorporated herein by reference in their entirety.

Independently, the first reactor vessel 110 and the second reactor vessel 130 can be configured for reforming temperatures that typically fall within the 350° C. to 600° C. range, such as, for example, from about 400° C. to about 600° C., or from about 425° C. to about 575° C. In one aspect, the first reactor vessel 110 can be configured for decreasing temperature from the first reactor inlet 105 to the first reactor outlet 115. Additionally or alternatively, the second reactor vessel 130 can be configured for decreasing temperature from the second reactor inlet 125 to the second reactor outlet 135. In these and other aspects, the first reactor vessel 110 and the second reactor vessel 130 can be configured for radial flow (i.e., the reactor vessels are radial flow reactors). However, the reactor vessels are not limited thereto. For instance, a traditional packed bed (or fixed bed) reactor can be employed as the first reactor vessel 110 and/or the second reactor vessel 130, in aspects of this invention.

Likewise, the first reactor vessel 110 and the second reactor vessel 130 can be configured, independently, for any suitable operating pressure, which can often be at least 20 psig (139 kPag), at least 25 psig (172 kPag), or at least 30 psig (207 kPag), and in some aspects, up to an operating pressure of as much as about 60 psig (414 kPag) to about 100 psig (689 kPag). Hence, typical operating pressures include from about 20 psig (139 kPag) to about 100 psig (689 kPag), or from about 25 psig (172 kPag) to about 60 psig (414 kPag). In some aspects, the reforming pressure in the first reactor vessel 110 can be greater than the reforming pressure in the second reactor vessel 130.

Additional information on features and designs of aromatization reactor vessels that can be employed in the aromatization reactor vessel systems described herein is disclosed in U.S. Pat. Nos. 6,548,030, 7,544,335, 7,582,272, 8,119, 203, and 9,085,736, which are incorporated herein by reference in their entirety.

The first reactor vessel 110 contains the first aromatization catalyst 112. The first aromatization catalyst 112 can comprise a first transition metal and a first catalyst support, and can be characterized by a first surface area in a range from about 80 $m^2/g$ to about 150 $m^2/g$, and a first micropore volume in a range from about 0.01 cc/g to about 0.048 cc/g. In some aspects, the first aromatization catalyst 112 can have a first surface area in a range from about 85 $m^2/g$ to about 140 $m^2/g$, or from about 90 $m^2/g$ to about 145 $m^2/g$, and a first micropore volume in a range from about 0.01 cc/g to about 0.045 cc/g, from about 0.015 cc/g to about 0.045 cc/g, or from about 0.02 cc/g to about 0.04 cc/g. Consistent with aspects of this invention, the first aromatization catalyst 112 can be a regenerated aromatization catalyst, although not limited thereto.

Likewise, the second reactor vessel 130 contains the second aromatization catalyst 132. The second aromatization catalyst 132 can comprise a second transition metal and a second catalyst support, and can be characterized by a second surface area in a range from about 160 $m^2/g$ to about 260 $m^2/g$, and a second micropore volume in a range from about 0.05 cc/g to about 0.09 cc/g. In some aspects, the second aromatization catalyst 132 can have a second surface area in a range from about 165 m²/g to about 240 m²/g, or from about 160 m²/g to about 220 m²/g, and a second micropore volume in a range from about 0.05 cc/g to about 0.085 cc/g, from about 0.055 cc/g to about 0.09 cc/g, or from about 0.06 cc/g to about 0.085 cc/g. Consistent with aspects of this invention, the second aromatization catalyst can be a fresh aromatization catalyst, although not limited thereto.

Typically, the first aromatization catalyst 112 can further contain a measurable amount of carbon, often ranging from about 0.01 wt. % to about 1 wt. %, from about 0.01 wt. % to about 0.5 wt. %, or from about 0.02 wt. % to about 0.5 wt. %. In contrast, the second aromatization catalyst 132 often contains no measurable amount of carbon, i.e., less than 0.01 wt. %, and more often, less than 0.005 wt. %. Therefore, and consistent with aspects of this invention, the first aromatization catalyst 112 can contain more carbon than does the second aromatization catalyst 132, often from about from about 0.01 wt. % to about 0.6 wt. % more, or from about 0.05 wt. % to about 0.5 wt. % more.

In further aspects of this invention, the first aromatization catalyst 112 can contain more iron than does the second aromatization catalyst 132. Additionally or alternatively, the first aromatization catalyst 112 can contain more sulfur than does the second aromatization catalyst 132 (e.g., the second aromatization catalyst can contain very low quantities of sulfur, i.e., less than 10 ppm). These comparisons are meant to be based on the relative amounts of iron (Fe) and sulfur (S) in ppm by weight of the respective catalysts. Additionally or alternatively, the first aromatization catalyst 112 can contain less nitrogen (N, in ppm by weight or wt. %) than does the second aromatization catalyst 132. In some aspects, the first aromatization catalyst 112 can contain less than 0.25 wt. % N, and in further aspects, the first aromatization catalyst 112 can contain no measurable amount of nitrogen.

Moreover, the first aromatization catalyst 112 can be characterized by a platinum dispersion that generally falls within a range from about 25% to about 65%, from about 25% to about 55%, or from about 30% to about 50%. In contrast, the second aromatization catalyst can be characterized by a platinum dispersion in a range from about 60% to about 75%, from about 60% to about 70%, or from about 65% to about 75%. Therefore, and consistent with aspects of this invention, the first aromatization catalyst 112 can have a lower platinum dispersion (%) than does the second aromatization catalyst 132, often from about from about 5% to about 40% less, or from about 10% to about 30% less.

Generally, the first aromatization catalyst can have a lower catalyst activity than that of the second aromatization catalyst. A lower catalyst activity can be determined by one or more of a higher TEOR (end of run temperature), a higher TSOR (start of run temperature), and a higher fouling rate. These performance metrics are described further in the examples that follow.

Generally, the first aromatization catalyst has a catalyst selectivity that is substantially the same as or better than that of the second aromatization catalyst, i.e., the selectivity is greater than or within about 2 percent of the selectivity of the second aromatization catalyst. The catalyst selectivity can be the aromatics selectivity and/or the benzene+toluene selectivity, as described further in the examples that follow.

While not being limited thereto, the weight ratio of the amount of the first aromatization catalyst 112 to the second aromatization catalyst 132 in the reactor vessel system 100 can be in a range (first:second) from about 20:1 to about 1:20, from about 15:1 to about 1:15, or from about 10:1 to about 1:10. In some aspects, the reactor vessel system 100 contains less of the first aromatization catalyst 112 than the second aromatization catalyst 132, and in these aspects, the first:second ratio can be in a range from about 1:1.5 to about 1:30, from about 1:2 to about 1:20, from about 1:3 to about 1:25, or from about 1:5 to about 1:15. For instance, it is contemplated that the reactor vessel system 100 can contain twice as much (or three times as much, or five times as much, or ten times as much) of the second aromatization catalyst 132, by weight, than the first aromatization catalyst 112.

As would be recognized by those of skill in the art, the features and characteristics of the first aromatization catalyst and the second aromatization catalyst (e.g., pore volume, amount of carbon, etc.) can vary as the time on stream of the reactor system increases. For instance, the features and characteristics of the first aromatization catalyst and the second aromatization catalyst can differ from start-up to after a long period of continuous production.

As it pertains to the first aromatization catalyst 112 and the second aromatization catalyst 132, the first catalyst support and the second catalyst support, independently, can comprise a zeolite. For instance, large pore zeolites often can have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often can have average pore diameters in a range of from about 5 Å to about 7 Å. The first catalyst support and the second catalyst support can be the same or different.

The term "zeolite" generally refers to a particular group of hydrated, crystalline aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically can be balanced by the inclusion of cations within the crystal, such as metals, alkali metals, alkaline earth metals, hydrogen, or combinations thereof.

In some aspects, the first catalyst support and/or the second catalyst support can comprise an L-type zeolite. L-type zeolite supports are a sub-group of zeolitic supports, which can contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, zinc, or combinations thereof, as well as non-metallic cations like hydronium and ammonium ions, which can be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one aspect, the first catalyst support and/or the second catalyst support can comprise a potassium L-type zeolite, also referred to as a KL-zeolite, while in another aspect, the first catalyst support and/or the second catalyst support can comprise a barium ion-exchanged L-zeolite. As used herein, the term "KL-zeolite" refers to L-type zeolites in which the principal cation M incorporated in the zeolite is potassium. A KL-zeolite can be cation-exchanged (for example, with barium) or impregnated with a transition metal and one or more halides to produce a transition metal impregnated, halided zeolite or a KL supported transition metal-halide zeolite catalyst.

In the first catalyst support and the second catalyst support, the zeolite can be bound with a support matrix (or binder), non-limiting examples of which can include silica, alumina, magnesia, boria, titania, zirconia, various clays, and the like, including mixed oxides thereof, as well as mixtures thereof. For example, the first catalyst support and/or the second catalyst support can comprise a binder comprising alumina, silica, a mixed oxide thereof, or a mixture thereof. The zeolite can be bound with the binder using any method known in the art. In a particular aspect of this invention, the first catalyst support, the second catalyst support, or both the first catalyst support and the second catalyst support, can comprise a silica-bound KL-zeolite catalyst support.

While not being limited thereto, the first catalyst support and the second catalyst support, independently, can comprise from about 5 wt. % to about 35 wt. % binder. For example, the first catalyst support and the second catalyst support, independently, can comprise from about 5 wt. % to about 30 wt. %, or from about 10 wt. % to about 30 wt. % binder. These weight percentages are based on the total weight of the (first or second) catalyst support.

The first aromatization catalyst can comprise a first transition metal and a first catalyst support, and the second aromatization catalyst can comprise a second transition metal and a second catalyst support. The first transition metal and the second transition metal can be the same or different, and can comprise a Group 7-11 transition metal or, alternatively, a Group 8-11 transition metal. In some aspects, the first aromatization catalyst and/or the second aromatization catalyst can comprise a Group 14 metal such as tin, while in other aspects, the first transition metal and/or the second transition metal can comprise a transition metal, and non-limiting examples of suitable transition metals can include iron, cobalt, nickel, ruthenium, rhodium, palladium, osmium, iridium, rhenium, platinum, gold, silver, copper, and the like, or a combination of two or more transition metals.

For example, the first aromatization catalyst and/or the second aromatization catalyst can comprise platinum, rhenium, tin, iron, gold, or any combination thereof. Alternatively, the first transition metal and/or the second transition metal can comprise a Group 7-11 transition metal (for example, one or more of platinum, rhenium, and gold), and in another aspect, the first transition metal and/or the second transition metal can comprise a Group 10 transition metal, while in yet another aspect, the first transition metal and the second transition metal can comprise platinum (Pt).

Typically, the first aromatization catalyst and the second aromatization catalyst can comprise from about 0.1 wt. % to about 10 wt. % transition metal. In another aspect, the first aromatization catalyst and/or the second aromatization catalyst can comprise from about 0.3 wt. % to about 5 wt. % transition metal. In yet another aspect, the first aromatization catalyst and/or the second aromatization catalyst can comprise from about 0.3 wt. % to about 3 wt. % transition metal, or from about 0.5 wt. % to about 2 wt. % transition metal. These weight percentages are based on the total weight of the (first or second) aromatization catalyst. In circumstances where the transition metal comprises platinum, the first aromatization catalyst and/or the second aromatization catalyst can comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum.

In an aspect, the first aromatization catalyst, the second aromatization catalyst, or both, can comprise platinum on a bound L-zeolite catalyst support. In another aspect, the first aromatization catalyst, the second aromatization catalyst, or both, can comprise platinum on a bound KL-zeolite catalyst support. In yet another aspect, the first aromatization catalyst, the second aromatization catalyst, or both, can comprise platinum on a silica-bound KL-zeolite catalyst support. Accordingly, the first aromatization catalyst and the second aromatization catalyst can be the same or different.

Additionally, the first aromatization catalyst and the second aromatization catalyst can further comprise a halogen, such as chlorine, fluorine, bromine, iodine, or a combination of two or more halogens. For example, the first aromatization catalyst and/or the second aromatization catalyst can comprise chlorine, or fluorine, or both chlorine and fluorine.

Chlorine can be present in the first aromatization catalyst, the second aromatization catalyst, or both, in an amount of from about 0.01 wt. % to about 5 wt. %, from about 0.1 wt. % to about 2 wt. %, or from about 0.3 wt. % to about 1.3 wt. %. Likewise, the first aromatization catalyst, the second aromatization catalyst, or both, can comprise from about 0.01 wt. % to about 5 wt. % fluorine, from about 0.1 wt. % to about 2 wt. % fluorine, or from about 0.3 wt. % to about 1.3 wt. % fluorine. These weight percentages are based on the total weight of the respective aromatization catalyst. In certain aspects, the first aromatization catalyst, the second aromatization catalyst, or both, comprise(s) chlorine and fluorine, and typically, the molar ratio of fluorine:chlorine, independently, can be in the range of from about 0.2:1 to about 4:1. Other suitable molar ratios of F:Cl can include the following non-limiting ranges: from about 0.3:1 to about 4:1, from about 0.5:1 to about 4:1, from about 0.2:1 to about 2:1, from about 0.3:1 to about 2:1, or from about 0.5:1 to about 2.5:1.

Examples of representative catalyst supports (e.g., zeolites and binders) and transition metals (e.g., platinum) that can be used as components of the first aromatization catalyst and/or the second aromatization catalyst include those disclosed in U.S. Pat. Nos. 5,196,631, 6,190,539, 6,406,614, 6,518,470, 6,812,180, 7,153,801, and 7,932,425, the disclosures of which are incorporated herein by reference in their entirety.

As disclosed herein, aromatization reactor vessel systems encompassed herein contain at least one first reactor vessel (which can comprise one first reactor vessel or a series of two or more first reactor vessels) and at least one second reactor vessel (which can comprise one second reactor vessel or a series of two or more second reactor vessels). For example, in addition to a system with a single first reactor vessel, exemplary reactor vessel systems can comprise any suitable number of first reactor vessels in series, such as from 2 to 8 vessels, from 2 to 4 vessels, from 2 to 3 vessels, 2 vessels, 3 vessels, or 4 vessels, in series. Likewise, in addition to a system with a single second reactor vessel, exemplary reactor vessel systems can comprise any suitable number of second reactor vessels in series, such as from 2 to 8 vessels, from 2 to 6 vessels, from 2 to 4 vessels, 3 vessels, 4 vessels, 5 vessels, 6 vessels, or 7 vessels, in series. The total number of reactor vessels in the aromatization reactor vessel systems is not particularly limited, but generally includes from 2 to 12 total vessels in series, such as from 2 to 10 vessels, from 2 to 8 vessels, from 2 to 6 vessels, from 2 to 5 vessels, 3 vessels, 4 vessels, 5 vessels, 6 vessels, or 7 vessels, in series. In some embodiments, the aromatization reactor vessel system encompasses a system wherein the at least one first reactor vessel comprises from 1 to 3 first reactor vessels in series, and the at least one second reactor vessel comprises from 2 to 6 second reactor vessels in series.

The reactor system can either be configured for a single pass of the non-aromatic hydrocarbon through the series of reactor vessels, or the reactor system can be configured to separate the unreacted non-aromatic hydrocarbons from the aromatic hydrocarbons, with subsequent recycling of the unreacted non-aromatic hydrocarbons to the first reactor vessel in the series.

The aromatization reactor vessel system can further comprise a furnace before any or each reactor vessel in the series, and the furnace can be capable of heating any feed stream to a reactor vessel operating temperature of from about 350° C. to about 600° C. Typically, the reactor vessel system contains a furnace before the first reactor vessel in the series. Also typically, the reactor vessel system contains a furnace before each reactor vessel in the series. Each furnace can be configured to heat a effluent of the previous reactor vessel in the series to a temperature of from about 350° C. to about 600° C. before entering the next vessel in the series. A transfer pipe can be positioned between and connect each furnace and respective upstream and downstream reactor vessel.

Figure 2:
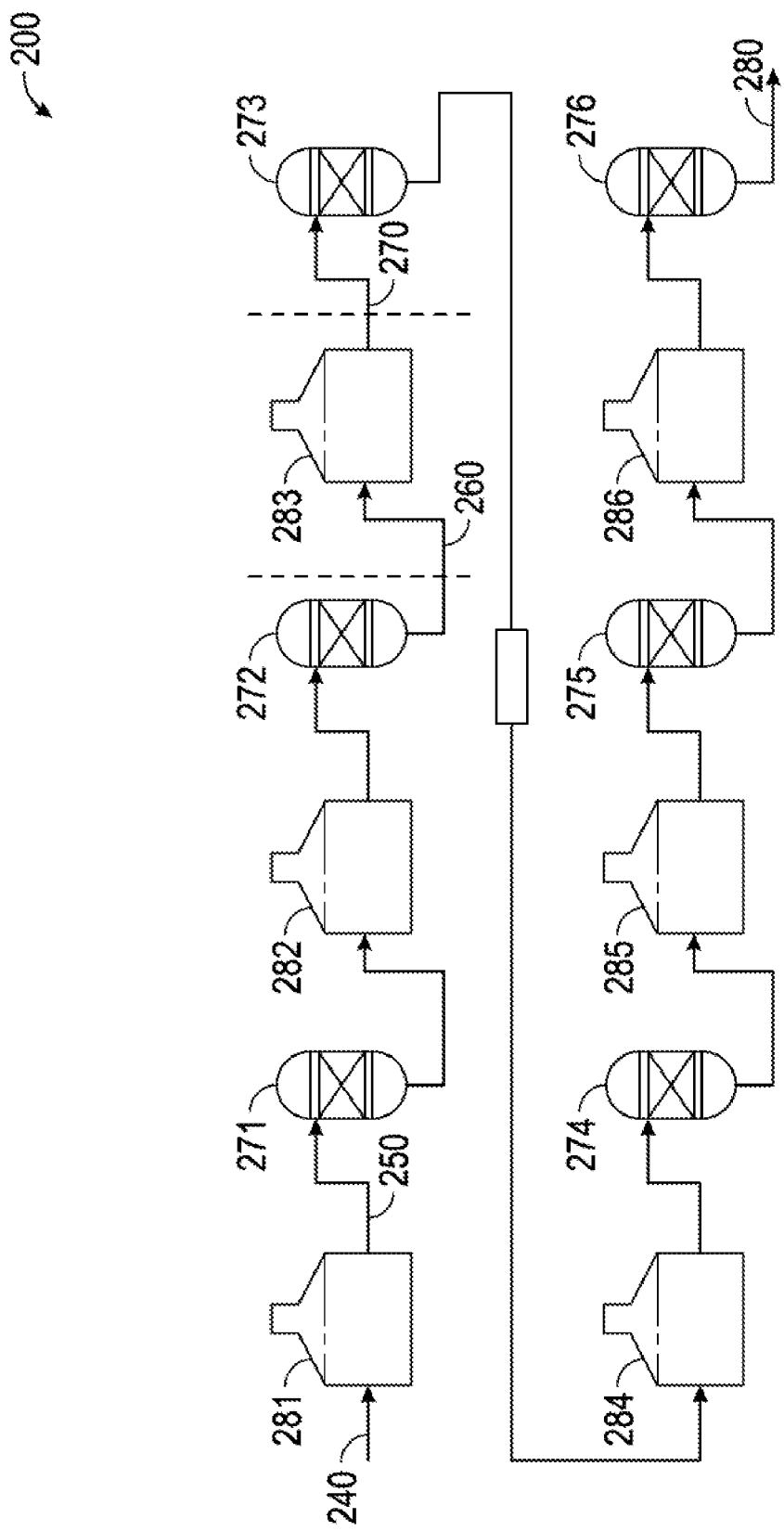
FIG. 2 illustrates a reactor system containing a series of furnaces and reactor vessels, in another aspect of the present invention.

FIG. 2 presents an illustrative example of an aromatization reactor vessel system 200 containing six reactor vessels 271, 272, 273, 274, 275, 276 in series, with a corresponding furnace 281, 282, 283, 284, 285, 286 preceding each respective reactor vessel in the system 200. The furnaces 281, 282, 283, 284, 285, 286 in FIG. 2 can be capable of heating or reheating any feed stream or effluent to a reactor vessel operating temperature of from about 350° C. to about 600° C.

In FIG. 2, the aromatization reactor vessel system 200 contains two (2) first reactor vessels 271, 272 in series, four (4) second reactor vessels 273, 274, 275, 276 in series, and a furnace 283 positioned between the first reactor vessels and the second reactor vessels. The first reactor vessels 271, 272 include a first reactor inlet 250 for introducing a first hydrocarbon feed into the first reactor vessels 271, 272, and a first reactor outlet 260 for discharging a first effluent that contains a first aromatic product. As described above in relation to FIG. 1, the first aromatization catalyst is present in each first reactor vessel.

Likewise, the second reactor vessels 273, 274, 275, 276 include a second reactor inlet 270 for introducing a second hydrocarbon feed into the second reactor vessels 273, 274, 275, 276, and a second reactor outlet 280 for discharging a second effluent that contains a second aromatic product. As described above in relation to FIG. 1, the second aromatization catalyst is present in each second reactor vessel.

The furnace 283 is positioned between the first reactor vessels and the second reactor vessels as shown in FIG. 2, specifically, between the first reactor outlet 260 and the second reactor inlet 270. The furnace 283 in FIG. 2 is capable of heating the first effluent (in the first reactor outlet 260 from the first reactor vessels) to form the second hydrocarbon feed (in the second reactor inlet 270 to the second reactor vessels). Generally, the furnace 283 is configured to heat the first effluent to a reforming temperature of any of the second reactor vessels 273, 274, 275, 276, often ranging from about 350° C. to about 600° C.

A feed stream 240 can enter the first furnace 281 of the aromatization reactor vessel system 200 shown in FIG. 2. Each reactor vessel in the system can be configured to contact the feed stream with an aromatization catalyst to catalytically convert at least a portion of the non-aromatic hydrocarbon to produce an aromatic hydrocarbon (for example, benzene, toluene, xylenes, and the like, as well as combinations thereof). Progressively more of the non-aromatic hydrocarbon is converted to the aromatic hydrocarbon, starting with the more easily converted non-aromatic hydrocarbons, as each reactor vessel in the series has been traversed. A final effluent 280 exits the last reactor vessel 276 in the system 200.

As an illustrative example, 10 wt. % of the total catalyst in the reactor system can be present in first reactor vessel 271, and 10 wt. % of the total catalyst can be present in first reactor vessel 272. In this example, the second reactor vessels 273, 274, 275, 276 can contain, respectively, 15 wt. %, 15 wt. %, 25 wt. %, and 25 wt. % of the total catalyst. Thus, the weight ratio of the amount of the first aromatization catalyst to the second aromatization catalyst in the reactor vessel system (first:second) is equal to 1:4, i.e., the reactor system contain four times as much of the second aromatization catalyst as compared to the first aromatization catalyst.

Aromatization Processes

Aspects of this invention also are directed to aromatization or reforming process. A representative aromatization process can comprise (or consist essentially of, or consist of) (i) introducing a first hydrocarbon feed into at least one first reactor vessel comprising a first aromatization catalyst, and contacting the first hydrocarbon feed with the first aromatization catalyst under first reforming conditions to produce a first aromatic product; wherein the first aromatization catalyst (e.g., a regenerated aromatization catalyst) comprises a first transition metal and a first catalyst support, the first aromatization catalyst characterized by a first surface area in a range from about 80 $m^2/g$ to about 150 $m^2/g$, and/or a first micropore volume in a range from about 0.01 cc/g to about 0.048 cc/g; (ii) discharging a first effluent comprising the first aromatic product from the at least one first reactor vessel; (iii) heating the first effluent to form a second hydrocarbon feed; (iv) introducing the second hydrocarbon feed into at least one second reactor vessel comprising a second aromatization catalyst, and contacting the second hydrocarbon feed with the second aromatization catalyst under second reforming conditions to produce a second aromatic product; wherein the second aromatization catalyst (e.g., a fresh aromatization catalyst) comprises a second transition metal and a second catalyst support, the second aromatization catalyst characterized by a second surface area in a range from about 160 $m^2/g$ to about 260 $m^2/g$, and/or a second micropore volume in a range from about 0.05 cc/g to about 0.09 cc/g; and (v) discharging a second effluent comprising the second aromatic product from the at least one second reactor vessel.

Generally, the features of the aromatization process (for example, the first and second hydrocarbon feed, the first and second aromatization catalyst, the first and second aromatic product, and the first and second surface areas and pore volumes, among others) are independently described herein and these features can be combined in any combination to further describe the disclosed aromatization processes. Moreover, other process steps can be conducted before, during, and/or after any of the steps listed in this aromatization process, unless stated otherwise.

In these processes, the first hydrocarbon feed and the second hydrocarbon feed, independently, can comprise naphtha (e.g., a mixture of hydrocarbons obtained from the distillation of petroleum). For instance, the first hydrocarbon feed can comprise non-aromatic hydrocarbons, such as $C_6$-$C_9$ alkanes and/or cycloalkanes, or $C_6$-$C_8$ alkanes and/or cycloalkanes. Typically, the first aromatic product formed in these aromatization processes can comprise benzene, toluene, or a combination thereof.

Since aromatic hydrocarbons are produced in the first reactor vessel(s), the second hydrocarbon feed contains, in addition to non-aromatic hydrocarbons, aromatic hydrocarbons formed in the first reactor vessel(s). Thus, the second hydrocarbon feed can comprise non-aromatic hydrocarbons—such as $C_6$-$C_9$ alkanes and/or cycloalkanes, or $C_6$-$C_8$ alkanes and/or cycloalkanes—and aromatic hydrocarbons—such as benzene and/or toluene. In like manner, the second aromatic product formed in these aromatization processes can comprise benzene, toluene, or a combination thereof.

Consistent with aspects of this invention, the first hydrocarbon feed typically contains relatively more convertible hydrocarbons (e.g., cyclohexane) than does the second hydrocarbon feed, when compared on a mole percent basis. While not wishing to be bound by the following theory, it is believed that the readily converted non-aromatic hydrocarbons have been converted to aromatic products in the first reactor vessel(s), prior to entering the second reactor vessel(s).

Suitable first reforming conditions and second reforming conditions, independently, can encompass the same ranges disclosed hereinabove in relation to the reactor vessel operating conditions. For example, the first reforming conditions and the second reforming conditions, independently, can comprise a reforming temperature in a range from about 350° C. to about 600° C. (or from about 400° C. to about 600° C.) and a reforming pressure in a range from about 20 psig (138 kPag) to about 150 psig (1034 kPag) (or from about 70 psig to about 120 psig (about 483 kPag to about 827 kPag)). While not required, often the reforming pressure in the first reactor vessel(s) is higher than in the second reactor vessel(s).

While not wishing to be bound by the following theory, it is believed that the first reforming conditions can include a lower $H_2$:hydrocarbon molar ratio than that utilized in the second reforming conditions, and that this difference can be due to hydrogen generation in the first reactor vessel(s).

Other suitable non-aromatic hydrocarbon feed materials, aromatic hydrocarbon products, and aromatization or reforming conditions for use in the disclosed process can be found, for example, in U.S. Pat. Nos. 4,456,527, 5,389,235, 5,401,386, 5,401,365, 6,207,042, 7,932,425, and 9,085,736, the disclosures of which are incorporated herein by reference in their entirety.

Referring now to the first aromatization catalyst and the second aromatization catalyst used in the disclosed aromatization processes, the first catalyst support and the second catalyst support can be the same or different and, independently, can be any of the catalyst supports disclosed herein as being suitable catalyst support materials for use in the first or second aromatization reactor vessels. For example, the first catalyst support and/or the second catalyst support can comprise a silica-bound KL-zeolite. Likewise, the first transition metal and the second transition metal, independently, can be any of the transition metals disclosed herein as being suitable transition metals for use in the first or second aromatization reactor vessels. For example, the first transition metal and the second transition metal can comprise platinum. Accordingly, the first aromatization catalyst and the second aromatization catalyst, independently, can comprise any suitable weight percentage of transition metal (or platinum) or an amount of transition metal (or platinum) in any range disclosed herein, for example, from about 0.1 wt. % to about 10 wt. %, from about 0.3 wt. % to about 5 wt. %, or from about 0.5 wt. % to about 2 wt. %, based on the total weight of the respective aromatization catalyst.

In one aspect, the first aromatization catalyst and/or the second aromatization catalyst can comprise platinum on a bound L-zeolite catalyst support, while in another aspect, the first aromatization catalyst and/or the second aromatization catalyst can comprise platinum on a bound KL-zeolite catalyst support, and in yet another aspect, the first aromatization catalyst and/or the second aromatization catalyst can comprise platinum on a silica-bound KL-zeolite catalyst support.

Independently, the first aromatization catalyst and the second aromatization catalyst can further comprise a halogen, such as chlorine and/or fluorine. Suitable amounts are disclosed herein, and often range from about 0.01 wt. % to about 5 wt. %, or from about 0.3 to about 1.3 wt. %, of fluorine and chlorine individually. The relative amount of fluorine and chlorine on the respective catalyst also is disclosed herein, and generally falls within a molar ratio range of fluorine:chlorine (F:Cl) from about 0.2:1 to about 4:1.

The first aromatization catalyst generally has less surface area and pore volume than the second aromatization catalyst. For instance, the first aromatization catalyst can have a surface area in a range from about 80 m$^2$/g to about 150 m$^2$/g, from about 85 m$^2$/g to about 140 m$^2$/g, or from about 90 m$^2$/g to about 145 m$^2$/g, while the second aromatization catalyst can have a surface area that typically falls within a range from about 160 m$^2$/g to about 260 m$^2$/g, from about 165 m$^2$/g to about 240 m$^2$/g, or from about 160 m$^2$/g to about 220 m$^2$/g. Similarly, the first micropore volume of the first aromatization catalyst can be from about 0.01 cc/g to about 0.048 cc/g, from about 0.01 cc/g to about 0.045 cc/g, from about 0.015 cc/g to about 0.045 cc/g, or from about 0.02 cc/g to about 0.04 cc/g, while the second micropore volume of the second aromatization catalyst typically falls within a range from about 0.05 cc/g to about 0.09 cc/g, from about 0.05 cc/g to about 0.085 cc/g, from about 0.055 cc/g to about 0.09 cc/g, or from about 0.06 cc/g to about 0.085 cc/g.

Furthermore, as described herein, the first aromatization catalyst often contains relatively more carbon (in wt. %), relatively more iron (in ppm by weight), relatively more sulfur (in ppm by weight), and/or relatively less nitrogen (in ppm by weight), than does the second aromatization catalyst. Additionally or alternatively, the first aromatization catalyst can be characterized by a lower platinum dispersion than that of the second aromatization catalyst.

Generally, the first aromatization catalyst can have a lower catalyst activity than that of the second aromatization catalyst. A lower catalyst activity can be determined by one or more of a higher TEOR (end of run temperature), a higher TSOR (start of run temperature), and a higher fouling rate. These performance metrics are described further in the examples that follow.

Generally, the first aromatization catalyst has a catalyst selectivity that is substantially the same as or better than that of the second aromatization catalyst, i.e., the selectivity is greater than or within about 2 percent of the selectivity of the second aromatization catalyst. The catalyst selectivity can be the aromatics selectivity and/or the benzene+toluene selectivity, as described further in the examples that follow. Moreover, any comparisons are meant to be performed under the same test conditions.

As would be recognized by those of skill in the art, the features and characteristics of the first aromatization catalyst and the second aromatization catalyst (e.g., pore volume, amount of carbon, etc.) can vary as the process is conducted for longer periods of time. For instance, the features and characteristics of the first aromatization catalyst and the second aromatization catalyst can differ from the start-up phase of the process to after a long period of continuous operation of the process.

While not being limited thereto, the weight ratio of the amount of the first aromatization catalyst to the second aromatization catalyst in the aromatization process (first: second) can range from about 20:1 to about 1:20, from about 15:1 to about 1:15, or from about 10:1 to about 1:10. However, the aromatization process can be conducted with significantly less of the first aromatization catalyst, as compared to the amount of the second aromatization catalyst, such that the first:second ratio can be in a range from about 1:1.5 to about 1:30, from about 1:2 to about 1:20, from about 1:3 to about 1:25, or from about 1:5 to about 1:15.

The aromatization process can be conducted with at least one first reactor vessel (which can comprise one first reactor vessel or a series of two or more first reactor vessels) and at least one second reactor vessel (which can comprise one second reactor vessel or a series of two or more second reactor vessels). For example, in addition a single first reactor vessel, the process can be performed with from 2 to 8 first reactor vessels, from 2 to 4 first reactor vessels, or from 2 to 3 first reactor vessels, in series. Likewise, in addition to a single second reactor vessel, the process can be performed with from 2 to 8 second reactor vessels, from 2 to 6 second reactor vessels, or from 2 to 4 second reactor vessels, in series.

The aromatization process is not limited by the reactor type. In one aspect, for instance, the first reactor vessel(s) and the second reactor vessel(s) can be radial flow reactors. Alternatively, the first reactor vessel(s) and the second reactor vessel(s) can be traditional packed bed (or fixed bed) reactors. Any hydrocarbon feed or effluent in the aromatization process can be heated to typical reforming temperatures with any suitable apparatus, such as a furnace.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Sulfur content was measured by inductively coupled plasma spectroscopy (ICP). Surface areas were determined using the Brunauer, Emmett, and Teller ("BET") method, described in Brunauer, Stephen; Emmett, P. H.; Teller, Edward (1938), "Adsorption of Gases in Multimolecular Layers," Journal of the American Chemical Society, 60 (2): 309-319, doi:10.1021/ja01269a023, which is incorporated herein by reference in its entirety. Micropore volumes were determined using the t-plot method using the thickness equation of Harkins and Jura. The t-plot method is described by Lippens and de Boer in Lippens B. C., and de Boer J. H., (1965), J. Catal. 4, 319; and De Boer J. H. Lippens B. C, Linsen B. G., Broeckhoff J. C. P., van den Heuvel A., and Onsinga T. V., (1966), J. Colloid Interf. Sci. 21, 405, each of which is incorporated herein by reference in its entirety. The thickness equation of Harkins and Jura is published in the Journal of the American Chemical Society, 66, 1366 (1944), which is incorporated herein by reference in its entirety. As used herein, micropores are defined as pores having pore diameters less than 2 nm, mesopores are defined as having pore diameters between 2 and 50 nm, and macropores are defined as pores having pore diameters greater than 50 nm. Platinum dispersion was determined by CO chemisorption.

Weight percentages of Pt, Cl, F, and Fe were determined using X-ray fluorescence (XRF), and are based on the total weight of the aromatization catalyst, unless stated otherwise. Carbon (wt. %) was determined by CHNS analyzer (Carlo Erba).

Examples 1-2

The fresh aromatization catalyst of Example 1 was a Pt/KL-zeolite containing approximately 1 wt. % platinum, 0.7-0.9 wt. % Cl and 0.7-0.9 wt. % F, and having a BET surface area of approximately 178 $m^2/g$ and a micropore volume of 0.062 cc/g.

For use in Example 2, the fresh catalyst of Example 1 was deactivated after contact with sulfur to form a sulfur-contaminated catalyst (a "spent" catalyst) containing 178 ppm by weight of sulfur. Prior to use in Example 2, the sulfur-contaminated aromatization catalyst was subjected to a hydrocarbon removal treatment to remove unreacted hydrocarbons and some light carbonaceous deposits from the sulfur-contaminated catalyst.

To regenerate the spent catalyst in Example 2, 100 g of the sulfur-contaminated catalyst were washed with deionized water containing KCl (0.1 M). The washing conditions consisted of 3 wash cycles, each conducted at 100° F. for 20 minutes with the weight of the wash water (excluding KCl) being 2.5 times the weight of the catalyst. The washing was performed batchwise with $N_2$ bubbling to agitate the mixture. The washed catalyst was next dried at 250° F. for 4 hours and calcined at 900° F. for 1 hour under air flow. For the halogenation step, 1.43 g of ammonium chloride and 1.82 g of ammonium fluoride were dissolved into 35 mL of deionized water. Next, 100 g of the washed catalyst were impregnated with the halogen solution. The impregnated material was allowed to soak for 4 hours at room temperature. It was then dried at 43 torr and 38° C. for 2 hours. The temperature was then increased to 95° C. for 1 hour. Lastly, the catalyst of Example 2 was calcined in flowing air at 900° F. for 1 hour.

For Example 1 and Example 2, the following standard testing procedures were utilized. The respective catalysts were ground and sieved to 25-45 mesh and 0.69 g (~1 cc) of the sieved catalyst was placed in a ⅜-inch OD stainless steel reactor vessel in a temperature controlled furnace. After reducing the catalyst under flowing molecular hydrogen, a feed stream of aliphatic hydrocarbons (12 mL/min) and molecular hydrogen (43 mL/min) was introduced to the reactor vessel at a pressure of 100 psig, a $H_2$:hydrocarbon molar ratio of 1.3, and a liquid hourly space velocity (LHSV) of 12 $hr^{-1}$ to obtain catalyst performance data over time. The hydrocarbon feed contained from 22 to 26 wt. % n-hexane, 4 to 8 wt. % n-heptane, 33 to 37 wt. % $C_6$ iso-paraffins, 15 to 21 wt. % $C_7$ iso-paraffins, 6 to 10 wt. % $C_8$ iso-paraffins, with the balance attributable to $C_6$ and $C_7$ olefins, naphthenes, $C_5$-species, and aromatics. The reactor effluent composition was analyzed by gas chromatography (using a capillary column and a flame ionization detector) to determine the amount of aromatics, such as benzene and toluene.

The catalysts of Example 1 and Example 2 were tested for their respective fouling rates (abbreviated FR, units of ° F./hr), which correlate to their activities by the formula, y=FR*t+TSOR, where y is temperature, FR is the fouling rate, t is time, and TSOR is the initial Start of Run temperature. The FR of a catalyst sample was determined by plotting the temperature (yield adjusted catalyst temperature) required to maintain a total yield of aromatics (such as benzene and toluene) at 63 wt. % over time at standard test conditions, as described above. The FR's were then determined from the calculated slopes fit to the resulting data using linear regression. The total time on stream was 40 hours, and the End of Run temperature (abbreviated TEOR) at 40 hours also was determined. In order to exclude the catalyst break-in period, only data from 15+ hours online was included in the TSOR and FR calculations.

Figure 3:
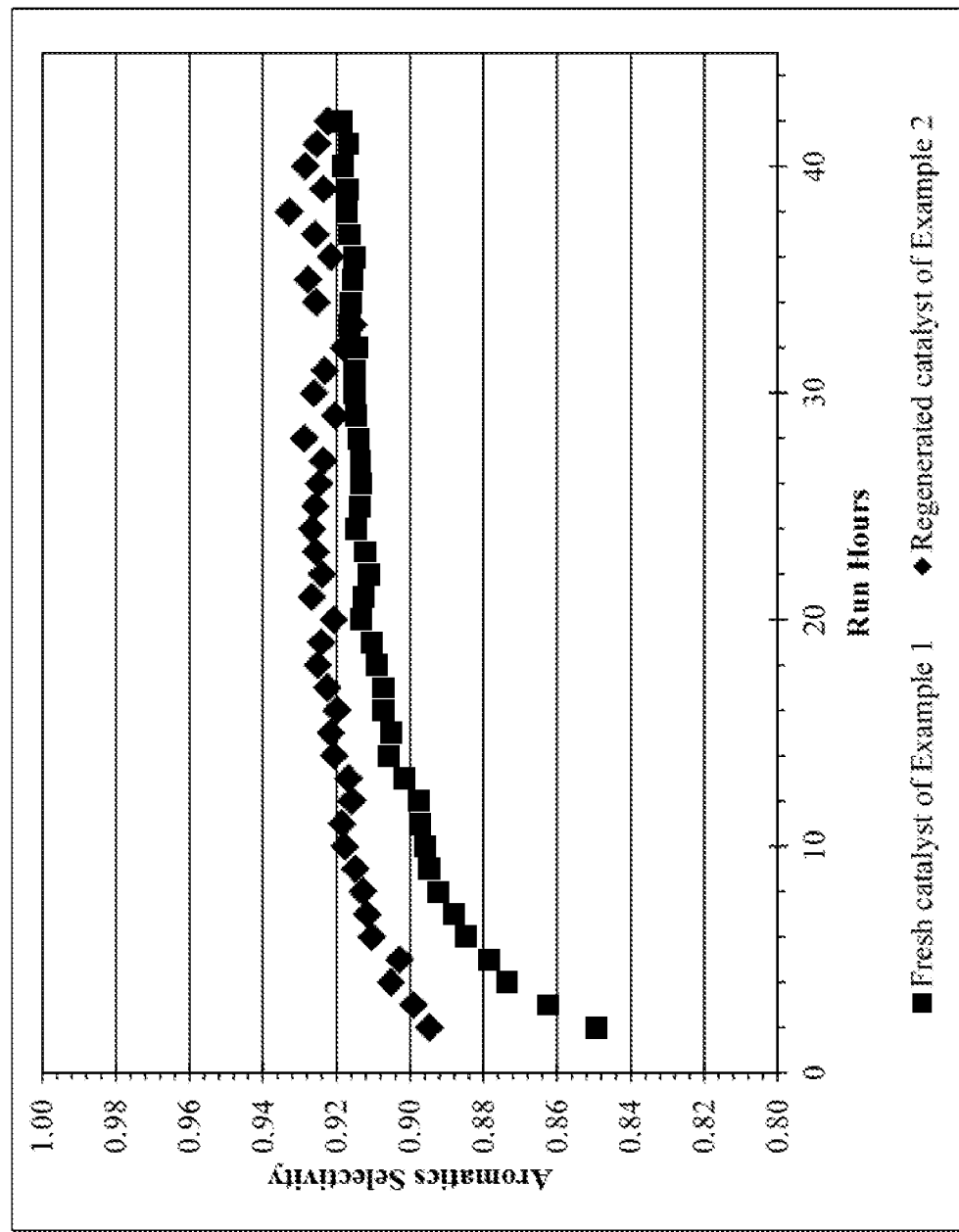
FIG. 3 presents a plot of the aromatics selectivity versus reaction time for the fresh catalyst of Example 1 and the regenerated catalyst of Example 2.
Figure 4:
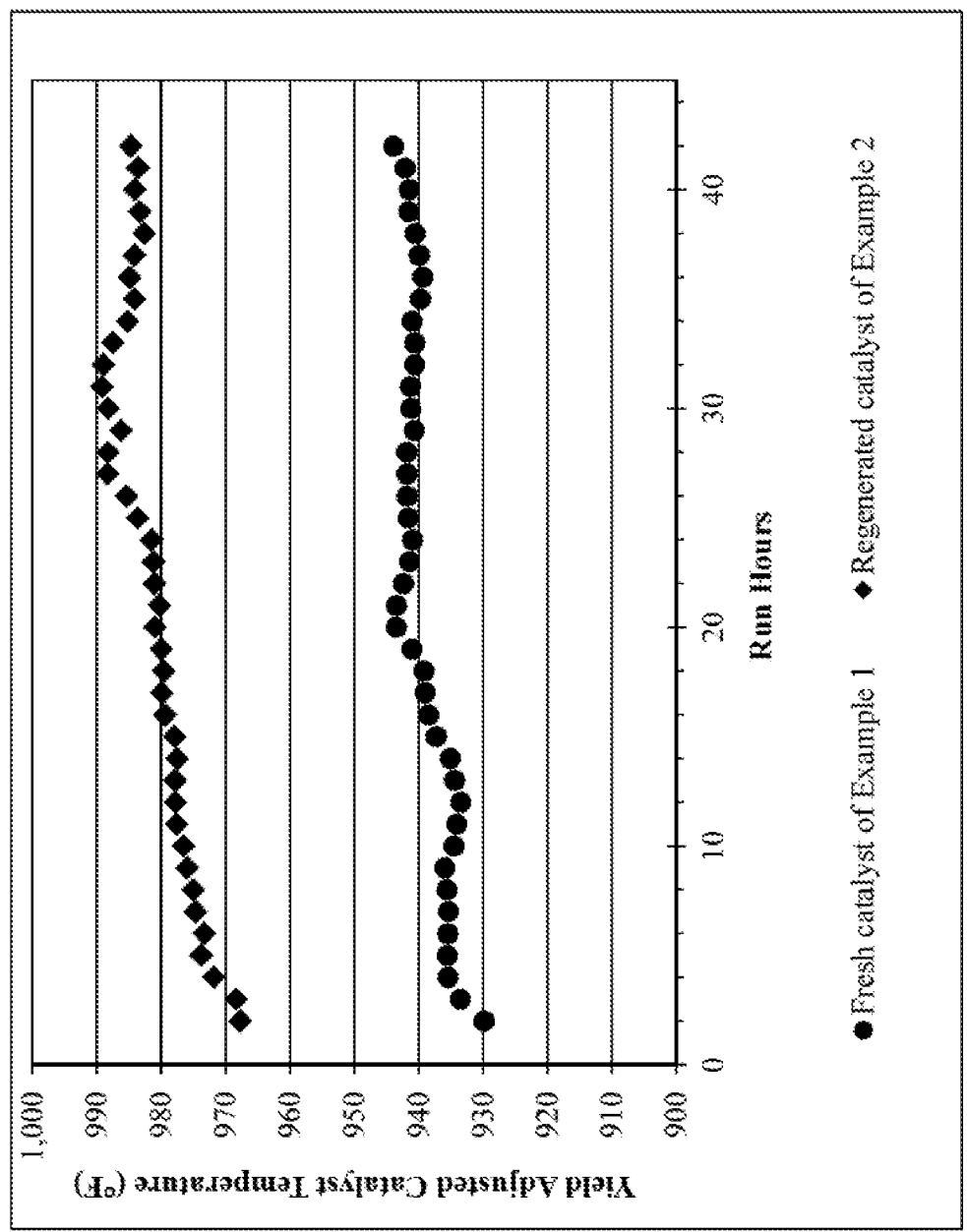
FIG. 4 presents a plot of the yield adjusted catalyst temperature versus reaction time for the fresh catalyst of Example 1 and the regenerated catalyst of Example 2.

FIG. 3 and FIG. 4, respectively, compare the aromatics selectivity and yield adjusted catalyst temperature versus the reaction time for the catalysts of Example 1 (fresh) and Example 2 (regenerated catalyst). Table I summarizes certain properties of the catalysts of Examples 1-2 and relevant performance metrics from FIGS. 3-4.

Notably, the regenerated catalyst of Example 2 had an aromatics selectivity equivalent to or better than that of the fresh catalyst of Example 1, despite having significantly lower surface area and micropore volume. The catalyst activity of Example 1 was superior to that of Example 2: lower TSOR, lower TEOR, and lower fouling rate. Examples 1-2 demonstrate that, while the catalyst selectivity was restored via regeneration (even with sulfur contamination), the catalyst activity of the regenerated catalyst was not equivalent to that of the fresh catalyst.

TABLE I

Examples 1-2.

| Example | 1 | 2 |
|---|---|---|
| Catalyst | Fresh | Regenerated |
| Platinum Dispersion (%) | 67 | 35 |
| Surface Area (m²/g) | 178 | 100 |
| Micropore Volume (cc/g) | 0.062 | 0.026 |
| Sulfur (ppmw) | N/A | 107 |
| Aromatics Yield at 1000° F. | >63% | >63% |
| TSOR (° F.) | 939 | 977 |
| TEOR (° F.) | 942 | 985 |
| Fouling Rate (° F./hr) | 0.05 | 0.23 |

Examples 3-5

The fresh aromatization catalyst of Example 3 was a Pt/KL-zeolite containing approximately 1 wt. % platinum, 0.83 wt. % Cl and 0.84 wt. % F, and having a BET surface area of approximately 177 m²/g, a total nitrogen pore volume of 0.19 cc/g, and a micropore volume of 0.062 cc/g.

For use in Examples 4-5, the fresh catalyst of Example 3 was deactivated after long-term use in an aromatization process (a "spent" catalyst). Prior to use in Examples 4-5, the spent catalyst was subjected to a hydrocarbon removal treatment to remove unreacted hydrocarbons and some light carbonaceous deposits from the spent catalyst.

To regenerate the spent catalyst in Example 4, the spent catalyst was dried under nitrogen at 400° F. (204° C.) for 16 hours (GHSV=1500 hr⁻¹). Chlorine diluted in a nitrogen gas stream (0.9 vol. % CO was added to the dried spent catalyst at 300° F. (149° C.) over 3 hours. After the chlorination step was complete, the chlorinated spent catalyst was purged at 400° F. (204° C.) with nitrogen for 16 hours. After purging, nitrogen gas was replaced by a mixture of air and nitrogen (1 vol. % oxygen). The catalyst was heated up to 750° F. (340° C.) for 44 hours using a 0.8° F./min ramp (0.4° C./min). After the carbon burn step, fluorine was added in the liquid phase. First, 0.69 g of ammonium fluoride was dissolved into 13 mL of deionized water, then 38 g of the chlorinated and de-coked catalyst was impregnated with the fluorine-containing solution at ambient temperature, followed by resting the impregnated catalyst for 4 hours. The fluorinated catalyst was dried for 3 hours under vacuum at a maximum temperature of 95° C., followed by calcination at 900° F. (482° C.) in air for 1 hour.

For Examples 3 and Example 4, the following standard testing procedures were utilized. The respective catalysts were ground and sieved to 25-45 mesh, and 1 cc of the sieved catalyst was placed in a ⅜-inch OD stainless steel reactor vessel in a temperature controlled furnace. After reducing the catalyst under flowing molecular hydrogen, a feed stream of aliphatic hydrocarbons and molecular hydrogen was introduced to the reactor vessel at a pressure of 100 psig, a H₂:hydrocarbon molar ratio of 1.3:1, and a liquid hourly space velocity (LHSV) of 12 hr⁻¹ to obtain catalyst performance data over time. The aliphatic hydrocarbon feed contained approximately 0.61 mole fraction of convertible $C_6$ species and 0.21 mole fraction of convertible $C_7$ species. The balance was attributed to aromatics, $C_8^+$, and highly branched isomers, which are classified as non-convertibles. The reactor effluent composition was analyzed by gas chromatography to determine the total aromatics and the aromatics selectivity.

Catalyst activity was quantified by the temperature needed to obtain a defined aromatics yield of 63 wt. % in $C_5^+$. The temperatures were then plotted versus time to evaluate catalyst activity performance over time. Lower temperatures, therefore, demonstrate a more active catalyst. Selectivity to aromatics (mol/mol) was calculated and also used to compare catalyst selectivity over time.

Figure 5:
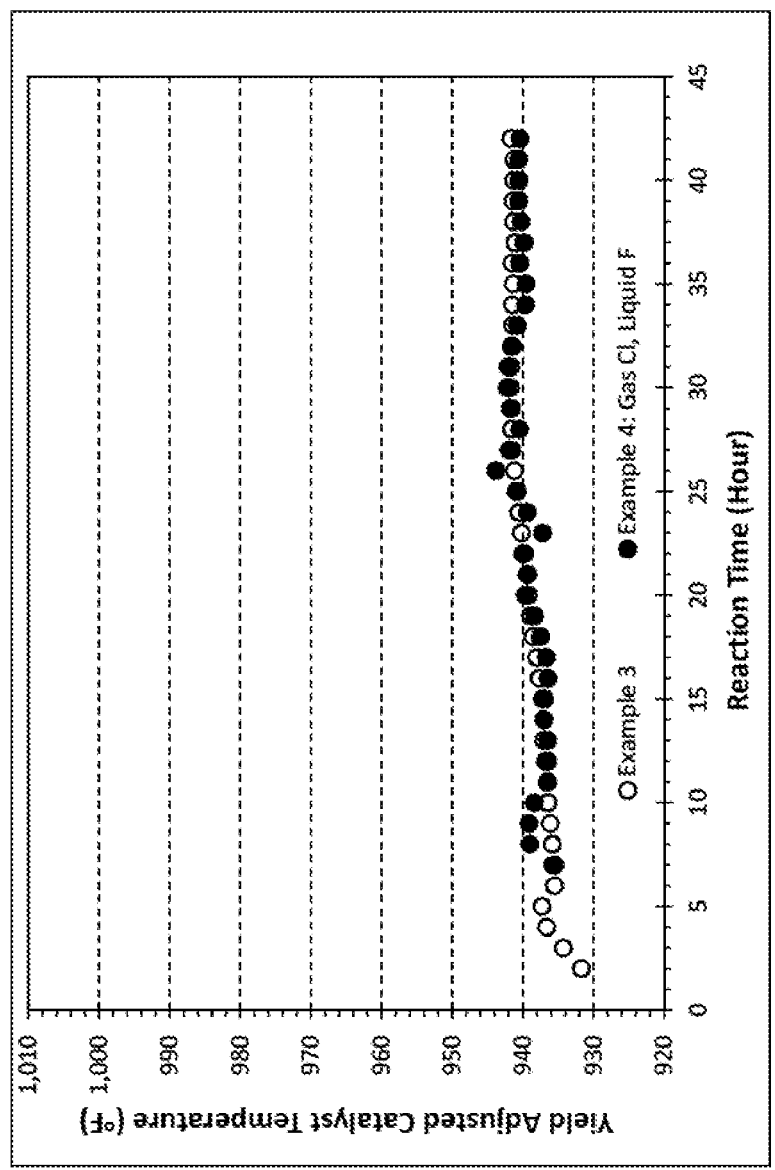
FIG. 5 presents a plot of the yield adjusted catalyst temperature versus reaction time for the fresh catalyst of Example 3 and the regenerated catalyst of Example 4.
Figure 6:
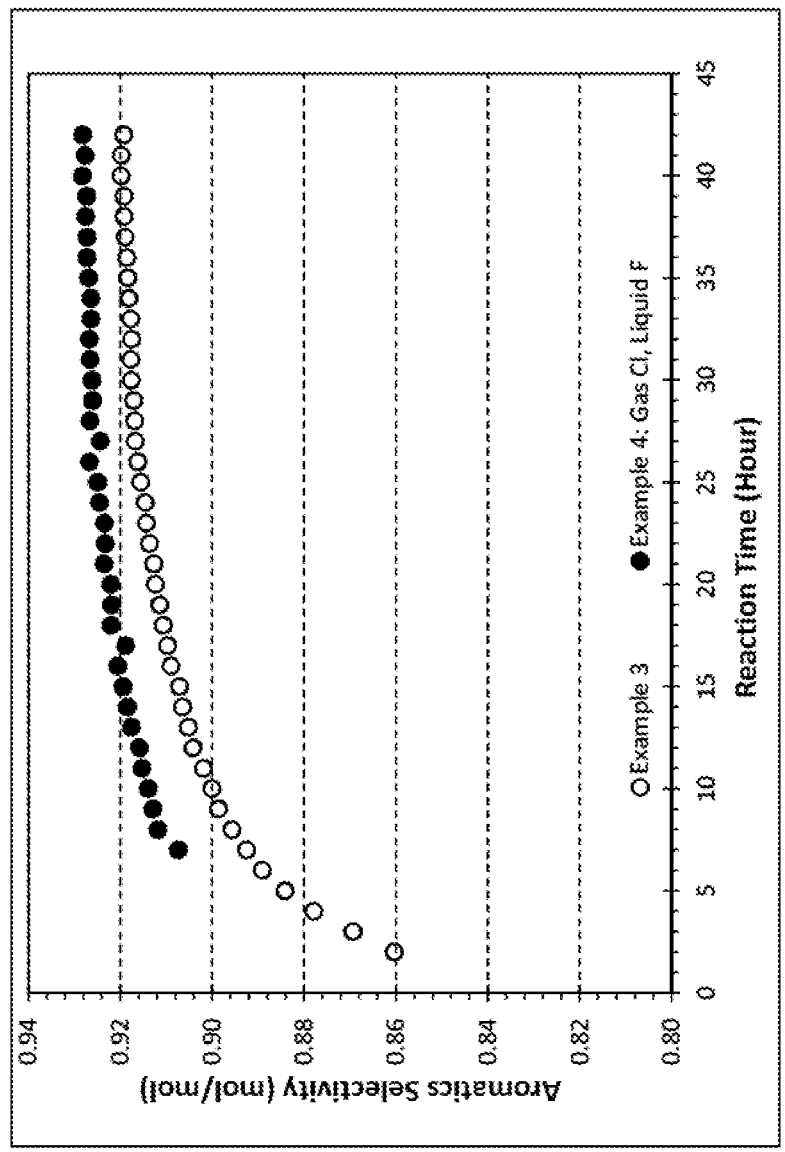
FIG. 6 presents a plot of the aromatics selectivity versus reaction time for the fresh catalyst of Example 3 and the regenerated catalyst of Example 4.

FIG. 5 illustrates that full catalyst activity can be restored for some regenerated catalysts: the catalyst activities for the fresh catalyst of Example 3 and the regenerated catalyst of Example 4 were substantially the same. Specifically, FIG. 5 shows that the same temperature was needed for both the fresh catalyst of Example 3 and the regenerated catalyst of Example 4 to achieve the same aromatics yield (63 wt. % in $C_5^+$) throughout the 40-hr experiment, indicating that the fresh catalyst and the regenerated catalyst had substantially the same catalyst activity. FIG. 6 illustrates that the catalyst selectivity of the regenerated catalyst of Example 4 was comparable to, or better than, that of the fresh catalyst of Example 3. Specifically, FIG. 6 shows aromatics selectivity in the 90-94% range for the regenerated catalyst of Example 4 throughout the 40-hr experiment, which was slightly better than that of the fresh catalyst.

Figure 7:
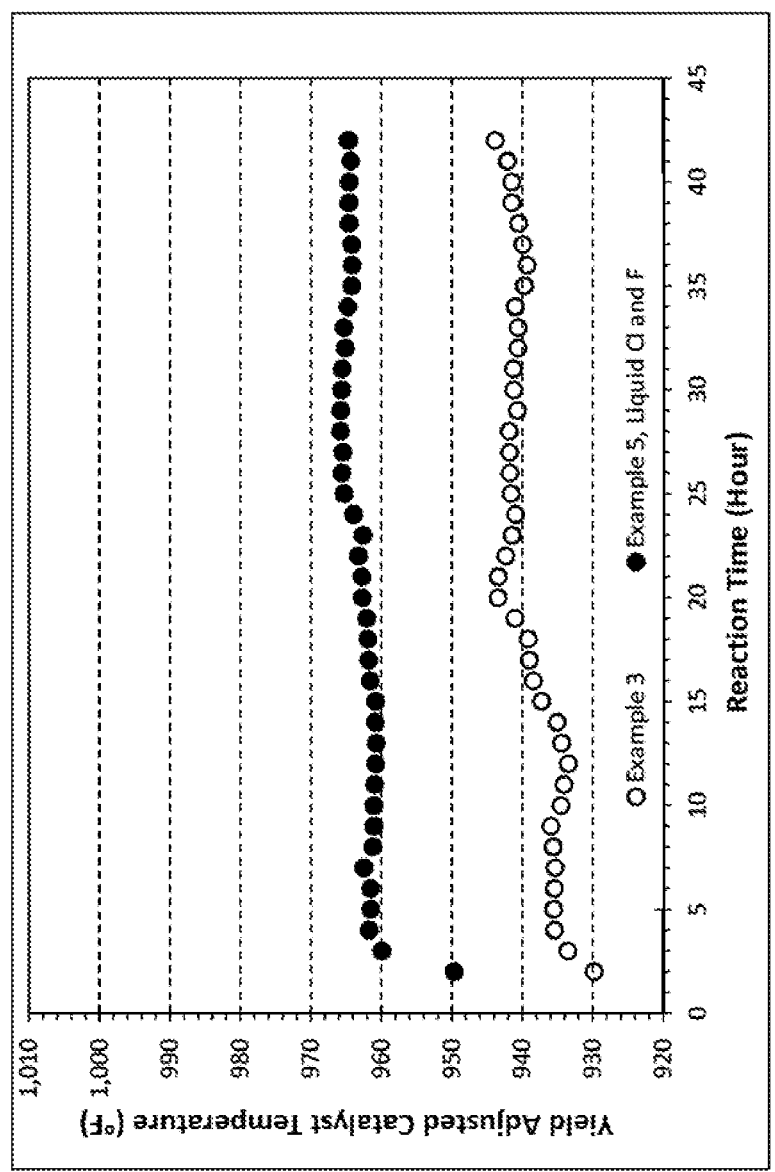
FIG. 7 presents a plot of the yield adjusted catalyst temperature versus reaction time for the fresh catalyst of Example 3 and the regenerated catalyst of Example 5.
Figure 8:
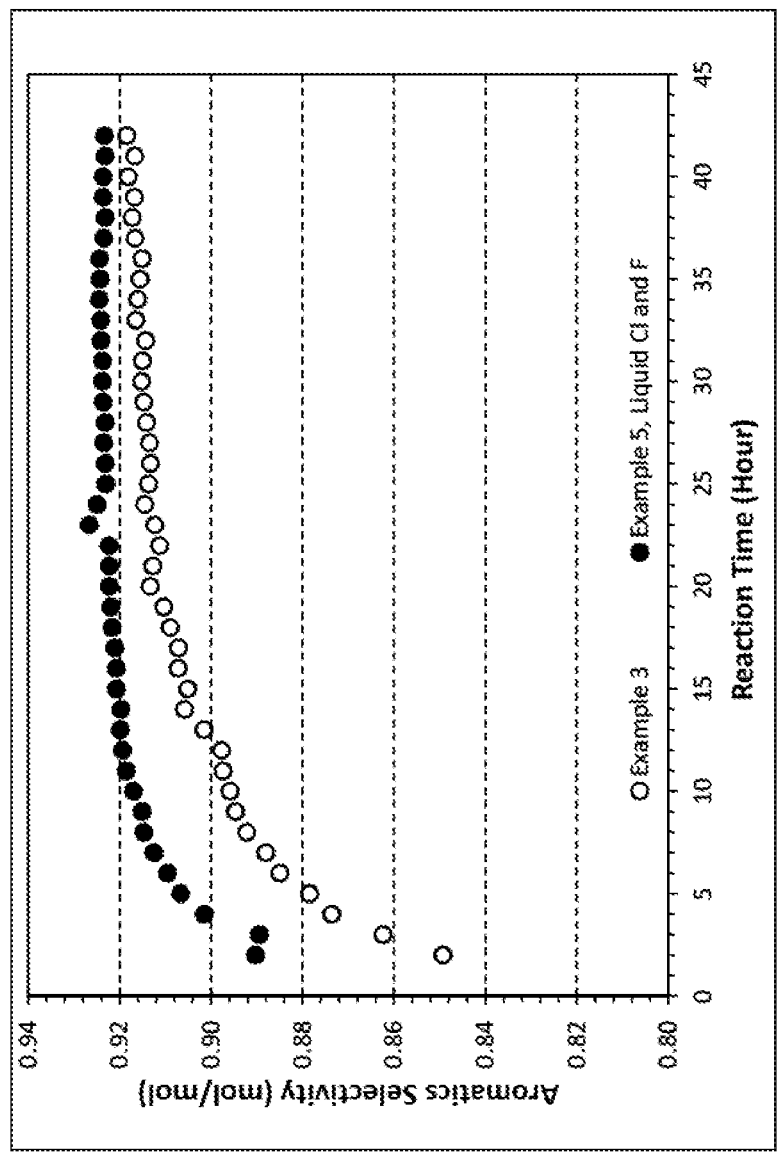
FIG. 8 presents a plot of the aromatics selectivity versus reaction time for the fresh catalyst of Example 3 and the regenerated catalyst of Example 5.

To regenerate the spent catalyst in Example 5, both chlorination and fluorination steps were performed in the liquid phase. First, 1.43 g of ammonium chloride and 1.82 g of ammonium fluoride were dissolved in 30 mL of deionized water, then 100 g of the spent catalyst was impregnated with the chlorine/fluorine-containing solution. The impregnated material was then vacuum dried at a maximum temperature of 95° C., followed by calcination in air at 900° F. (482° C.) for 1 hour using a 550° F./h ramp (288° C./h). The regenerated catalyst of Example 5 was then tested in the aromatization reaction using the same procedure as Examples 3-4. FIGS. 7-8 demonstrate that selectivity was restored to the regenerated catalyst of Example 5, but the activity of the regenerated catalyst of Example 5 was far less than that of the fresh catalyst of Example 3 (~20-25° F. higher temperatures were needed to achieve 63 wt. % aromatics yield).

Certain properties of the catalysts of Examples 3-5 are summarized in Table II. In sum, the data from FIGS. 5-8 and Table II indicate that the catalyst selectivity was restored via regeneration, but the catalyst activity was not always recoverable. Interestingly, despite the much lower platinum dispersion and micropore volume values for Examples 4-5, the catalyst selectivity for Examples 4-5 was comparable to, if not better than that of the fresh catalyst of Example 3.

TABLE II

Examples 3-5.

| Property | Example 5 | Example 4 | Example 3 |
|---|---|---|---|
| Micropore volume (cc/g) | 0.038 | 0.030 | 0.062 |
| Pt Dispersion (%) | 38 | 48 | 67 |
| Carbon (wt. %) | 0.01 | 0.02 | 0.01 |
| Fluorine (wt. %) | 0.69 | 0.63 | 0.84 |
| Chlorine (wt. %) | 0.89 | 0.89 | 0.83 |

Examples 6-7

The fresh aromatization catalyst of Example 6 was a Pt/KL-zeolite containing approximately 1 wt. % platinum, 0.85 wt. % Cl, and 0.70 wt. % F, and having a BET surface area of approximately 177.5 m²/g, a total nitrogen pore volume of 0.19 cc/g, and a micropore volume of 0.0615 cc/g.

For use in Example 7, the fresh catalyst of Example 6 was deactivated after long-term use in an aromatization process (a "spent" catalyst). Prior to use in Example 7, the spent catalyst was subjected to a hydrocarbon removal treatment to remove unreacted hydrocarbons and some light carbonaceous deposits from the spent catalyst.

Example 7 used the following regeneration procedure. Approximately 42 g of the spent catalyst was charged to a new metal fixed-bed reactor (stainless steel 347), then contacted at 400° F. with a nitrogen gas stream (1500 mL/min) for 12 hr, then contacted at 400° F. with a chlorine-containing gas stream containing nitrogen (1463 mL/min) and chlorine gas (37 mL/min) for 3 hr, then contacted at 400° F. with a nitrogen gas stream (1463 mL/min) for 3 hr, then contacted at 750° F. with a decoking gas stream containing a mixture of air (75 mL/min) and nitrogen (1425 mL/min) for 44 hr, then contacted at 400° F. with a fluorine-containing gas stream containing nitrogen (1350 mL/min) and fluorine gas (147 mL/min) for 3 hr, and then contacted at 400° F. with a nitrogen gas stream (1353 mL/min) for 3 hr.

For Example 6 and Example 7, the following standard testing procedures were utilized. The catalysts were ground and sieved to about 25-45 mesh, and 1 g of the sieved catalyst was placed in a ¼-inch OD stainless steel reactor vessel in a temperature controlled furnace. After reducing the catalyst under flowing molecular hydrogen, a feed stream of aliphatic hydrocarbons and molecular hydrogen was introduced to the reactor vessel at a feed rate of 22 mL/min, a pressure of 100 psig, a $H_2$:hydrocarbon molar ratio of 1.3:1, and a liquid hourly space velocity (LHSV) of 12 $hr^{-1}$ to obtain catalyst performance data over time. The aliphatic hydrocarbon feed contained from 22 to 26 wt. % n-hexane, 4 to 8 wt. % n-heptane, 33 to 37 wt. % $C_6$ iso-paraffins, 17 to 21 wt. % $C_7$ iso-paraffins, 6 to 10 wt. % $C_8$ iso-paraffins, with the balance attributable to $C_6$ and $C_7$ olefins, naphthenes, and aromatics. The reactor effluent composition was analyzed by gas chromatography to determine the total aromatics and the benzene+toluene selectivity.

Catalyst activity and selectivity were monitored over a 40-hr experiment in which the temperature was adjusted to maintain a total aromatics yield at 63 wt. % over time at the standard test conditions, as described above.

Figure 9:
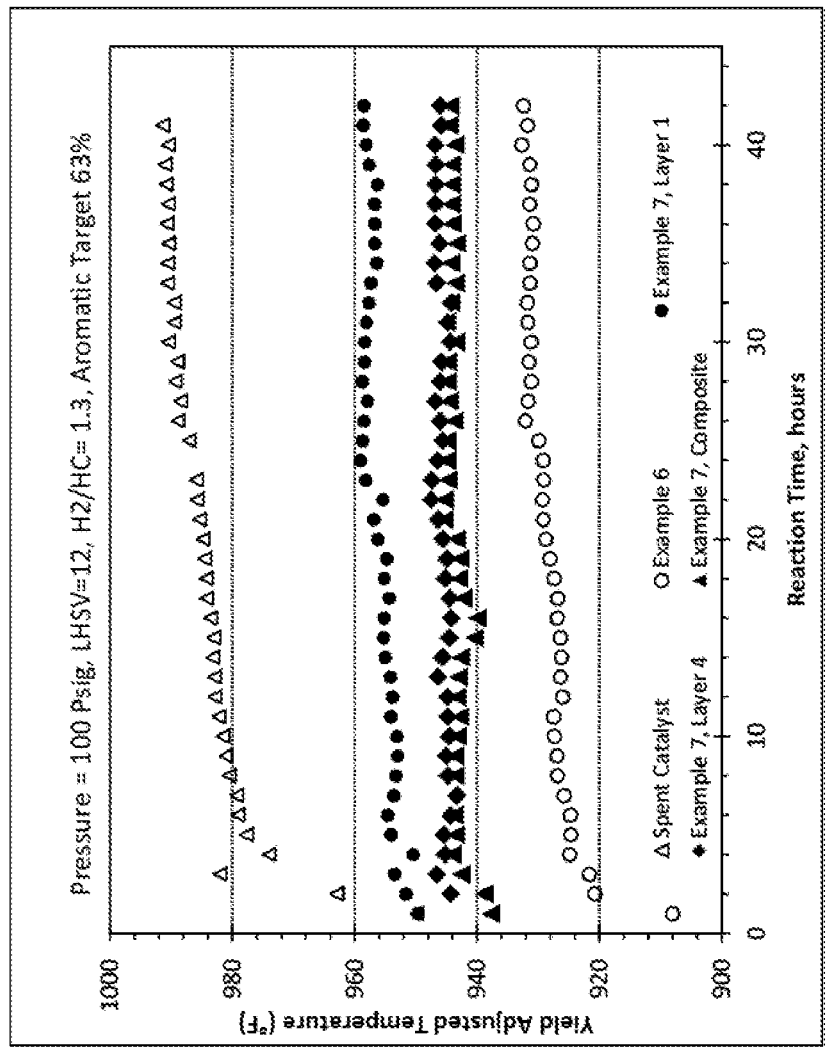
FIG. 9 presents a plot of the yield adjusted catalyst temperature versus reaction time for the spent catalyst, the fresh catalyst of Example 6, and the regenerated catalyst of Example 7.
Figure 10:
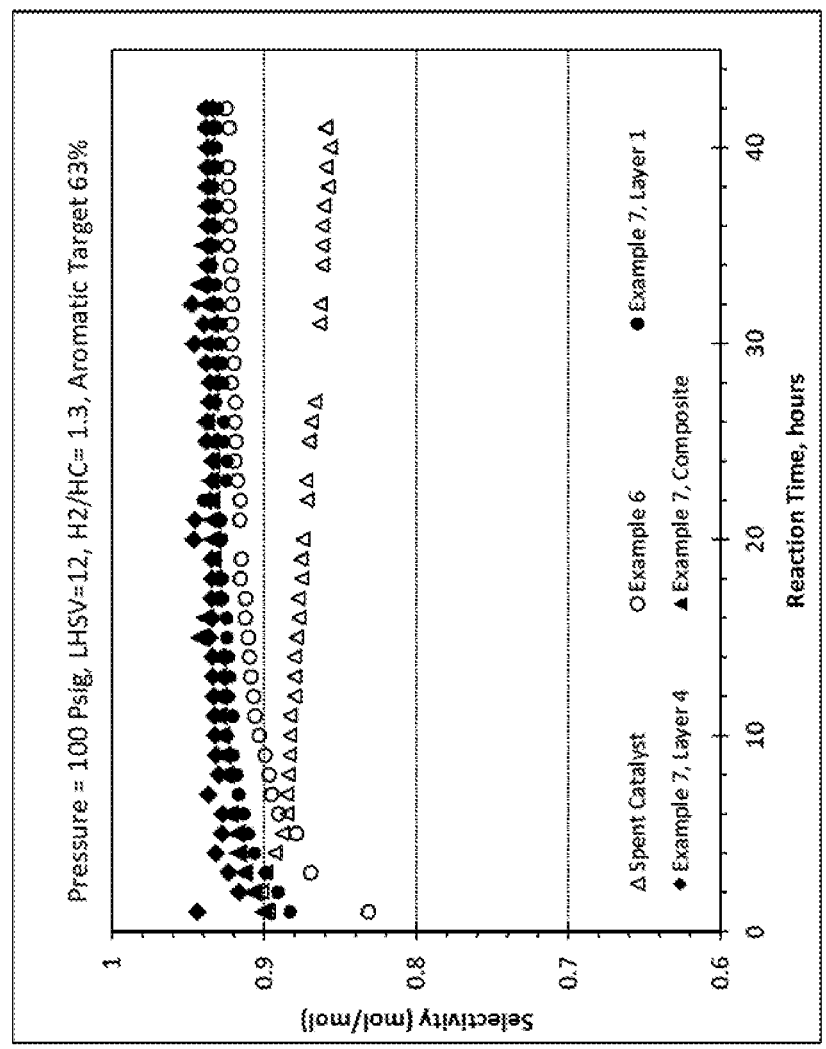
FIG. 10 presents a plot of the benzene+toluene selectivity versus reaction time for the spent catalyst, the fresh catalyst of Example 6, and the regenerated catalyst of Example 7.

FIG. 9 and FIG. 10 are plots of the yield adjusted temperature versus reaction time and the benzene+toluene selectivity versus reaction time, respectively, for the regenerated catalyst of Example 7 compared with the fresh catalyst of Example 6 and the spent catalyst. Table III summarizes certain properties of the regenerated catalyst of Example 7. In Table III, the amounts of Cl and F on the regenerated catalyst are in wt. %, the amount of carbon is in wt. %, and the amount of iron is in ppmw (ppm by weight). The fresh catalyst of Example 6 contained substantially no carbon and iron. After the regeneration process, the catalyst bed was split into four layers: Layer 1 was the top layer, Layer 4 was the bottom layer, and a composite was a physical mix of Layers 1-4.

In sum, the data from FIGS. 9-10 and Table III indicate that selectivity was restored via regeneration, but the activity of the regenerated catalyst was not equivalent to that of the fresh catalyst (higher temperatures were required to achieve the same aromatics yield). Interestingly, despite the iron and carbon levels of the regenerated catalyst of Example 7, the benzene+toluene selectivity for Example 7 was comparable to, if not better than that of the fresh catalyst of Example 6.

TABLE III

Example 7.

| Layer | Cl (wt. %) | F (wt. %) | Fe (ppmw) | Carbon (wt. %) |
|---|---|---|---|---|
| Layer 1 | 0.86 | 2.29 | 200 | 0.10 |
| Layer 2 | 0.95 | 1.06 | 189 | 0.07 |
| Layer 3 | 0.95 | 0.62 | 190 | 0.08 |
| Layer 4 | 0.94 | 0.12 | 195 | 0.12 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. An aromatization process comprising:

(i) introducing a first hydrocarbon feed into at least one first reactor vessel comprising a first aromatization catalyst, and contacting the first hydrocarbon feed with the first aromatization catalyst under first reforming conditions to produce a first aromatic product; wherein:

the first aromatization catalyst comprises a first transition metal and a first catalyst support, the first aromatization catalyst characterized by:

a first surface area in a range from about 80 m²/g to about 150 m²/g; and/or a first micropore volume in a range from about 0.01 cc/g to about 0.048 cc/g;

(ii) discharging a first effluent comprising the first aromatic product from the at least one first reactor vessel;

(iii) heating the first effluent to form a second hydrocarbon feed;

(iv) introducing the second hydrocarbon feed into at least one second reactor vessel comprising a second aromatization catalyst, and contacting the second hydrocarbon feed with the second aromatization catalyst under second reforming conditions to produce a second aromatic product; wherein:

the second aromatization catalyst comprises a second transition metal and a second catalyst support, the second aromatization catalyst characterized by:

a second surface area in a range from about 160 m²/g to about 260 m²/g; and/or a second micropore volume in a range from about 0.05 cc/g to about 0.09 cc/g; and (v) discharging a second effluent comprising the second aromatic product from the at least one second reactor vessel.

Aspect 2. The process of aspect 1, wherein the first aromatization catalyst has a first surface area in any range disclosed herein (e.g., from about 85 m²/g to about 140 m²/g), and the second aromatization catalyst has a second surface area in any range disclosed herein (e.g., from about 165 m²/g to about 240 m²/g).

Aspect 3. The process of any one of the preceding aspects, wherein the first aromatization catalyst has a first micropore volume in any range disclosed herein (e.g., from about 0.015 cc/g to about 0.045 cc/g), and the second aromatization catalyst has a second micropore volume in any range disclosed herein (e.g., from about 0.055 cc/g to about 0.09 cc/g).

Aspect 4. The process of any one of the preceding aspects, wherein the first aromatization catalyst contains more carbon (e.g., from about 0.01 wt. % to about 0.6 wt. % more carbon) than that of the second aromatization catalyst.

Aspect 5. The process of any one of the preceding aspects, wherein the first aromatization catalyst is further characterized by an amount of carbon in any range disclosed herein (e.g., from about 0.01 to about 1 wt. %), and the second aromatization catalyst is further characterized by an amount of carbon in any range disclosed herein (e.g., less than 0.01 wt. %, or no measurable amount).

Aspect 6. The process of any one of the preceding aspects, wherein the first aromatization catalyst contains less nitrogen (ppmw) than that of the second aromatization catalyst (e.g., the first aromatization catalyst may contain no measurable amount of nitrogen), and/or the first aromatization catalyst contains more sulfur (ppmw) than that of the second aromatization catalyst (e.g., the second aromatization catalyst may contain less than 10 ppm of sulfur).

Aspect 7. The process of any one of the preceding aspects, wherein the first aromatization catalyst contains more iron (Fe, ppmw) than that of the second aromatization catalyst.

Aspect 8. The process of any one of the preceding aspects, wherein the first aromatization catalyst has a lower platinum dispersion (e.g., from 10% to 30% lower) than that of the second aromatization catalyst.

Aspect 9. The process of any one of the preceding aspects, wherein the first aromatization catalyst is further characterized by a platinum dispersion in any range disclosed herein (e.g., from about 25% to about 65%, or from about 30% to about 50%), and the second aromatization catalyst is further characterized by a platinum dispersion in any range disclosed herein (e.g., from about 60% to about 75%).

Aspect 10. The process of any one of the preceding aspects, wherein the first aromatization catalyst has a lower catalyst activity than that of the second aromatization catalyst.

Aspect 11. The process of any one of the preceding aspects, wherein the first aromatization catalyst has a catalyst selectivity that is substantially the same as or better than that of the second aromatization catalyst.

Aspect 12. The process of any one of the preceding aspects, wherein a weight ratio the first aromatization catalyst to the second aromatization catalyst in the aromatization process is in any range of first:second disclosed herein, e.g., from about 1:1.5 to about 1:30, from about 1:2 to about 1:20, or from about 1:5 to about 1:15.

Aspect 13. The process of any one of the preceding aspects, wherein the at least one first reactor vessel and the at least one second reactor vessel are radial flow reactors.

Aspect 14. The process of any one of the preceding aspects, wherein the at least one first reactor vessel comprises a number of reactor vessels in any range disclosed herein (e.g., from 1 to 3 first reactor vessels in series), and the at least one second reactor vessel comprises a number of reactor vessels in any range disclosed herein (e.g., from 2 to 6 second reactor vessels in series).

Aspect 15. The process of any one of the preceding aspects, wherein the first hydrocarbon feed and the second hydrocarbon feed, independently, comprise naphtha.

Aspect 16. The process of any one of the preceding aspects, wherein the first hydrocarbon feed comprises non-aromatic hydrocarbons, e.g., $C_6$-$C_9$ alkanes and/or cycloalkanes, or $C_6$-$C_8$ alkanes and/or cycloalkanes.

Aspect 17. The process of any one of the preceding aspects, wherein the first aromatic product comprises benzene, toluene, or a combination thereof.

Aspect 18. The process of any one of the preceding aspects, wherein the second hydrocarbon feed comprises non-aromatic hydrocarbons (e.g., $C_6$-$C_9$ alkanes and/or cycloalkanes, or $C_6$-$C_8$ alkanes and/or cycloalkanes) and aromatic hydrocarbons (e.g., benzene and/or toluene).

Aspect 19. The process of any one of the preceding aspects, wherein the second aromatic product comprises benzene, toluene, or a combination thereof.

Aspect 20. The process of any one of the preceding aspects, wherein the first hydrocarbon feed contains more convertible hydrocarbons (e.g., cyclohexane) than the second hydrocarbon feed, on a mole percent basis.

Aspect 21. The process of any one of the preceding aspects, wherein the first reforming conditions and the second reforming conditions, independently, comprise a reforming temperature in any reforming temperature range disclosed herein, e.g., from about 350° C. to about 600° C., or from about 400° C. to about 600° C.

Aspect 22. The process of any one of the preceding aspects, wherein the first reforming conditions and the second reforming conditions, independently, comprise a reforming pressure in any reforming pressure range disclosed herein, e.g., from about 20 to about 100 psig.

Aspect 23. The process of any one of the preceding aspects, wherein the first reforming conditions comprise a higher reforming pressure than the second reforming conditions.

Aspect 24. The process of any one of the preceding aspects, wherein the first reforming conditions comprise a lower $H_2$:hydrocarbon molar ratio than the second reforming conditions.

Aspect 25. The process of any one of the preceding aspects, wherein the first catalyst support and the second catalyst support, independently, comprise a zeolite.

Aspect 26. The process of any one of the preceding aspects, wherein the first catalyst support and the second catalyst support, independently, comprise an L-zeolite, a Y-zeolite, a mordenite, an omega zeolite, and/or a beta zeolite.

Aspect 27. The process of any one of the preceding aspects, wherein the first catalyst and the second catalyst support, independently, comprise a potassium L-zeolite or a barium ion-exchanged L-zeolite.

Aspect 28. The process of any one of the preceding aspects, wherein the first catalyst support and the second catalyst support, independently, comprise a binder comprising alumina, silica, a mixed oxide thereof, or a mixture thereof.

Aspect 29. The process of any one of the preceding aspects, wherein the first catalyst support and the second catalyst support, independently, comprise any weight percentage of binder disclosed herein, e.g., from about 3 wt. % to about 35 wt. %, or from about 5 wt. % to about 30 wt. % binder, based on the total weight of the respective catalyst support.

Aspect 30. The process of any one of the preceding aspects, wherein the first catalyst support and the second catalyst support, independently, comprise a silica-bound KL-zeolite catalyst support.

Aspect 31. The process of any one of the preceding aspects, wherein the first transition metal and the second transition metal, independently, comprise a Group 7-11 transition metal, or a Group 8-11 transition metal.

Aspect 32. The process of any one of the preceding aspects, wherein the first transition metal and the second transition metal, independently, comprise platinum, rhenium, gold, or combinations thereof.

Aspect 33. The process of any one of the preceding aspects, wherein the first transition metal and the second transition metal comprise platinum.

Aspect 34. The process of any one of the preceding aspects, wherein the first aromatization catalyst and the second aromatization catalyst, independently, comprise any weight percentage range of (first or second) transition metal disclosed herein, e.g., from about 0.1 wt. % to about 10 wt. %, or from about 0.3 wt. % to about 5 wt. %, transition metal.

Aspect 35. The process of any one of the preceding aspects, wherein the first aromatization catalyst and the second aromatization catalyst, independently, comprise any weight percentage range of platinum disclosed herein, e.g., from about 0.1 wt. % to about 10 wt. %, or from about 0.5 wt. % to about 2 wt. %, platinum.

Aspect 36. The process of any one of the preceding aspects, wherein the first aromatization catalyst and the second aromatization catalyst, independently, comprise platinum on a bound L-zeolite catalyst support.

Aspect 37. The process of any one of the preceding aspects, wherein the first aromatization catalyst and the second aromatization catalyst, independently, comprise platinum on a bound KL-zeolite catalyst support.

Aspect 38. The process of any one of the preceding aspects, wherein the first aromatization catalyst and the second aromatization catalyst, independently, comprise platinum on a silica-bound KL-zeolite catalyst support.

Aspect 39. The process of any one of the preceding aspects, wherein the first aromatization catalyst and the second aromatization catalyst further comprise chlorine and fluorine.

Aspect 40. The process of any one of the preceding aspects, wherein the first aromatization catalyst and the second aromatization catalyst, independently, comprise any weight percentage range of chlorine and/or weight percentage range of fluorine disclosed herein, e.g., from about 0.01 wt. % to about 5 wt. %, or from about 0.3 to about 1.3 wt. % fluorine, and/or from about 0.01 wt. % to about 5 wt. %, or from about 0.3 to about 1.3 wt. % chlorine.

Aspect 41. The process of any one of the preceding aspects, wherein the first aromatization catalyst and the second aromatization catalyst, independently, comprise any molar ratio of fluorine:chlorine disclosed herein, e.g., from about 0.2:1 to about 4:1.

Aspect 42. The process of any one of the preceding aspects, wherein heating the first effluent is performed in any suitable apparatus, e.g., a furnace.

Aspect 43. The process of any one of the preceding aspects, wherein the at least one first reactor vessel comprises two or more reactor vessels in series, with a furnace between each reactor vessel.

Aspect 44. The process of any one of the preceding aspects, wherein the at least one second reactor vessel comprises two or more reactor vessels in series, with a furnace between each reactor vessel.

Aspect 45. An aromatization reactor vessel system comprising:

(A) at least one first reactor vessel comprising:

(a1) a first reactor inlet for introducing a first hydrocarbon feed into the at least one first reactor vessel;

(a2) a first aromatization catalyst for catalytically converting at least a portion of the first hydrocarbon feed under first reforming conditions to produce a first aromatic product; wherein the first aromatization catalyst comprises a first transition metal and a first catalyst support; the first aromatization catalyst characterized by:

a first surface area in a range from about 80 $m^2/g$ to about 150 $m^2/g$; and/or a first micropore volume in a range from about 0.01 cc/g to about 0.048 cc/g; and (a3) a first reactor outlet for discharging a first effluent comprising the first aromatic product from the at least one first reactor vessel;

(B) at least one second reactor vessel comprising:

(b1) a second reactor inlet for introducing a second hydrocarbon feed into the at least one second reactor vessel;

(b2) a second aromatization catalyst for catalytically converting at least a portion of the second hydrocarbon feed under second reforming conditions to produce a second aromatic product; wherein the second aromatization catalyst comprises a second transition metal and a second catalyst support, the second aromatization catalyst characterized by:

a second surface area in a range from about 160 $m^2/g$ to about 260 $m^2/g$; and/or a second micropore volume in a range from about 0.05 cc/g to about 0.09 cc/g; and (b3) a second reactor outlet for discharging a second effluent comprising the second aromatic product from the at least one second reactor vessel; and (C) a furnace positioned between the first reactor outlet and the second reactor inlet, the furnace capable of heating the first effluent to form the second hydrocarbon feed.

Aspect 46. The system of aspect 45, wherein the at least one first reactor vessel and the at least one second reactor vessel, independently, comprise stainless steel.

Aspect 47. The system of aspect 45 or 46, wherein the at least one first reactor vessel and the at least one second reactor vessel, independently, are configured for an operating pressure in any suitable range or in any range disclosed herein, e.g., at least 20 psig, at least 30 psig, or from about 20 to about 100 psig.

Aspect 48. The system of any one of aspects 45-47, wherein the at least one first reactor vessel and the at least one second reactor vessel, independently, comprise a coating/layer comprising any suitable metal or any metal disclosed herein (e.g., tin) that provides resistance to carburization and metal dusting.

Aspect 49. The system of any one of aspects 45-48, wherein the at least one first reactor vessel and the at least one second reactor vessel, independently, are configured for decreasing temperature from the (first or second) reactor inlet to the (first or second) reactor outlet.

Aspect 50. The system of any one of aspects 45-49, wherein the at least one first reactor vessel and the at least one second reactor vessel are radial flow reactors.

Aspect 51. The system of any one of aspects 45-50, wherein the at least one first reactor vessel and the at least one second reactor vessel are configured for a catalytic conversion of a non-aromatic hydrocarbon to an aromatic hydrocarbon (e.g., benzene, toluene, or xylenes).

Aspect 52. The system of any one of aspects 45-51, wherein the first catalyst support and the second catalyst support, independently, comprise a zeolite.

Aspect 53. The system of any one of aspects 45-52, wherein the first catalyst support and the second catalyst support, independently, comprise an L-zeolite, a Y-zeolite, a mordenite, an omega zeolite, and/or a beta zeolite.

Aspect 54. The system of any one of aspects 45-53, wherein the first catalyst support and the second catalyst support, independently, comprise a potassium L-zeolite or a barium ion-exchanged L-zeolite.

Aspect 55. The system of any one of aspects 45-54, wherein the first catalyst support and the second catalyst support, independently, comprise a binder comprising alumina, silica, a mixed oxide thereof, or a mixture thereof.

Aspect 56. The system of any one of aspects 45-55, wherein the first catalyst support and the second catalyst support, independently, comprise a silica-bound KL-zeolite catalyst support.

Aspect 57. The system of any one of aspects 45-56, wherein the first transition metal and the second transition metal, independently, comprise a Group 7-11 transition metal, or a Group 8-11 transition metal.

Aspect 58. The system of any one of aspects 45-57, wherein the first transition metal and the second transition metal, independently, comprise platinum, rhenium, gold, or combinations thereof.

Aspect 59. The system of any one of aspects 45-58, wherein the first transition metal and the second transition metal comprise platinum.

Aspect 60. The system of any one of aspects 45-59, wherein the first aromatization catalyst and the second aromatization catalyst, independently, comprise platinum on a bound L-zeolite catalyst support.

Aspect 61. The system of any one of aspects 45-60, wherein the first aromatization catalyst and the second aromatization catalyst, independently, comprise platinum on a bound KL-zeolite catalyst support.

Aspect 62. The system of any one of aspects 45-61, wherein the first aromatization catalyst and the second aromatization catalyst, independently, comprise platinum on a silica-bound KL-zeolite catalyst support.

Aspect 63. The system of any one of aspects 45-62, wherein the first aromatization catalyst and the second aromatization catalyst further comprise chlorine and fluorine.

Aspect 64. The system of any one of aspects 45-63, wherein the first aromatization catalyst has a first surface area in any range disclosed herein (e.g., from about 85 $m^2/g$ to about 140 $m^2/g$), and the second aromatization catalyst has a second surface area in any range disclosed herein (e.g., from about 165 $m^2/g$ to about 240 $m^2/g$).

Aspect 65. The system of any one of aspects 45-64, wherein the first aromatization catalyst has a first micropore volume in any range disclosed herein (e.g., from about 0.015 cc/g to about 0.045 cc/g), and the second aromatization catalyst has a second micropore volume in any range disclosed herein (e.g., from about 0.055 cc/g to about 0.09 cc/g).

Aspect 66. The system of any one of aspects 45-65, wherein the first aromatization catalyst contains more carbon (e.g., from about 0.01 wt. % to about 0.6 wt. %) than that of the second aromatization catalyst.

Aspect 67. The system of any one of aspects 45-66, wherein the first aromatization catalyst is further characterized by an amount of carbon in any range disclosed herein (e.g., from about 0.01 to about 1 wt. %), and the second aromatization catalyst is further characterized by an amount of carbon in any range disclosed herein (e.g., less than 0.01 wt. %, or no measurable amount).

Aspect 68. The system of any one of aspects 45-67, wherein the first aromatization catalyst contains less nitrogen (ppmw) than that of the second aromatization catalyst.

Aspect 69. The system of any one of aspects 45-68, wherein the first aromatization catalyst contains more iron (Fe, ppmw) and/or more sulfur (ppmw) than that of the second aromatization catalyst.

Aspect 70. The system of any one of aspects 45-69, wherein the first aromatization catalyst has a lower platinum dispersion (%) than that of the second aromatization catalyst.

Aspect 71. The system of any one of aspects 45-70, wherein the first aromatization catalyst is further characterized by a platinum dispersion in any range disclosed herein (e.g., from about 25% to about 65%, or from about 30% to about 50%), and the second aromatization catalyst is further characterized by a platinum dispersion in any range disclosed herein (e.g., from about 60% to about 75%).

Aspect 72. The system of any one of aspects 45-71, wherein the first aromatization catalyst has a lower catalyst activity than that of the second aromatization catalyst.

Aspect 73. The system of any one of aspects 45-72, wherein the first aromatization catalyst has a catalyst selectivity that is substantially the same as or better than that of the second aromatization catalyst.

Aspect 74. The system of any one of aspects 45-73, wherein a weight ratio of the first aromatization catalyst to the second aromatization catalyst in the reactor vessel system is in any range of first:second disclosed herein, e.g., from about 1:1.5 to about 1:30, from about 1:2 to about 1:20, or from about 1:5 to about 1:15.

Aspect 75. The system of any one of aspects 45-74, wherein the system comprises a number of at least one first reactor vessels in any range disclosed herein (e.g., from 1 to 3 first reactor vessels in series), and the system comprises a number of at least one second reactor vessels in any range disclosed herein (e.g., from 2 to 6 second reactor vessels in series).

Aspect 76. The system of any one of aspects 45-75, wherein the system comprises any suitable number of total reactor vessels in series or any number of reactor vessels in series disclosed herein, e.g., from 2 to 8 vessels in series, or 6 vessels in series.

Aspect 77. The system of any one of aspects 45-76, wherein the at least one first reactor vessel and the at least one second reactor vessel, independently, are configured for a reforming temperature in any reforming temperature range disclosed herein, e.g., from about 350° C. to about 600° C., or from about 400° C. to about 600° C.

Aspect 78. The system of any one of aspects 45-77, wherein the furnace is configured to heat the first effluent to a reforming temperature of the at least one second reactor vessel of from about 350° C. to about 600° C.

We claim:

1. An aromatization process comprising:
   (i) introducing a first hydrocarbon feed into at least one first reactor vessel comprising a first aromatization catalyst, and contacting the first hydrocarbon feed with the first aromatization catalyst under first reforming conditions to produce a first aromatic product; wherein:
   the first aromatization catalyst comprises platinum and a first catalyst support, the first aromatization catalyst characterized by:
   a first surface area in a range from about 80 $m^2/g$ to about 150 $m^2/g$; and/or
   a first micropore volume in a range from about 0.01 cc/g to about 0.048 cc/g;
   (ii) discharging a first effluent comprising the first aromatic product from the at least one first reactor vessel;
   (iii) heating the first effluent to form a second hydrocarbon feed;
   (iv) introducing the second hydrocarbon feed into at least one second reactor vessel comprising a second aromatization catalyst, and contacting the second hydrocarbon feed with the second aromatization catalyst under second reforming conditions to produce a second aromatic product; wherein:
   the second aromatization catalyst comprises platinum and a second catalyst support, the second aromatization catalyst characterized by:
   a second surface area in a range from about 160 $m^2/g$ to about 260 $m^2/g$; and/or
   a second micropore volume in a range from about 0.05 cc/g to about 0.09 cc/g; and
   (v) discharging a second effluent comprising the second aromatic product from the at least one second reactor vessel, wherein:
   the first catalyst support and the second catalyst support comprise a KL-zeolite and a binder comprising alumina, silica, a mixed oxide thereof, or a mixture thereof;
   the first aromatization catalyst and the second aromatization catalyst further comprise chlorine and fluorine;
   the first aromatization catalyst is a regenerated catalyst;
   the first aromatization catalyst has a lower platinum dispersion than that of the second aromatization catalyst; and
   the first aromatization catalyst has an aromatics selectivity that is substantially the same as or better than that of the second aromatization catalyst.

2. The process of claim 1, wherein:
   the first surface area is in a range from about 85 $m^2/g$ to about 140 $m^2/g$;
   the first micropore volume is in a range from about 0.015 cc/g to about 0.045 cc/g;
   the second surface area is in a range from about 165 $m^2/g$ to about 240 $m^2/g$; and
   the second micropore volume is in a range from about 0.05 cc/g to about 0.085 cc/g.

3. The process of claim 1, wherein a weight ratio of the first aromatization catalyst to the second aromatization catalyst is in a range from about 1:2 to about 1:20.

4. The process of claim 1, wherein the first aromatization catalyst contains more carbon, more sulfur, and/or more iron than that of the second aromatization catalyst.

5. The process of claim 1, wherein the first aromatization catalyst has from 10% to 30% lower platinum dispersion than that of the second aromatization catalyst.

6. The process of claim 1, wherein:
   the first aromatization catalyst is characterized by a platinum dispersion in a range from about 30% to about 50%; and
   the second aromatization catalyst is characterized by a platinum dispersion in a range from about 60% to about 75%.

7. The process of claim 1, wherein:
   the at least one first reactor vessel comprises from 1 to 3 first reactor vessels in series; and
   the at least one second reactor vessel comprises from 2 to 6 second reactor vessels in series.

8. The process of claim 1, wherein:
   the first aromatization catalyst has a lower catalyst activity than that of the second aromatization catalyst; and/or
   the first aromatization catalyst has a benzene+toluene selectivity that is substantially the same as or better than that of the second aromatization catalyst.

9. The process of claim 8, wherein:
   the first aromatization catalyst comprises from about 0.3 wt. % to about 5 wt. % of platinum; and
   the second aromatization catalyst comprises from about 0.3 wt. % to about 5 wt. % of platinum.

10. The process of claim 1, wherein:
    the first aromatic product and the second aromatic product, independently, comprise benzene, toluene, or a combination thereof; and
    the first reforming conditions and the second reforming conditions, independently, comprise a reforming temperature in a range from about 350° C. to about 600° C.

11. The process of claim 1, wherein the at least one first reactor vessel and the at least one second reactor vessel are radial flow reactors.

12. The process of claim 1, wherein a weight ratio of the first aromatization catalyst to the second aromatization catalyst is in a range from about 1:5 to about 1:15.

13. The process of claim 1, wherein the first aromatization catalyst and the second aromatization catalyst, independently, comprise from about 0.3 wt. % to about 5 wt. % of platinum.

14. The process of claim 13, wherein:
    the first surface area is in a range from about 85 $m^2/g$ to about 140 $m^2/g$;
    the first micropore volume is in a range from about 0.02 cc/g to about 0.04 cc/g;
    the second surface area is in a range from about 160 $m^2/g$ to about 220 $m^2/g$; and
    the second micropore volume is in a range from about 0.055 cc/g to about 0.09 cc/g.

15. The process of claim 13, wherein:
    a weight ratio of the first aromatization catalyst to the second aromatization catalyst is in a range from about 1:2 to about 1:20;
    the first aromatization catalyst has from 10% to 30% lower platinum dispersion than that of the second aromatization catalyst; and
    the first aromatic product and the second aromatic product, independently, comprise benzene, toluene, or a combination thereof.

16. The process of claim 13, wherein:

the first aromatization catalyst is characterized by a platinum dispersion in a range from about 30% to about 50%; and the second aromatization catalyst is characterized by a platinum dispersion in a range from about 60% to about 75%.

17. The process of claim 13, wherein:

the first aromatization catalyst has a lower catalyst activity than that of the second aromatization catalyst; and the first aromatization catalyst has a benzene+toluene selectivity that is substantially the same as or better than that of the second aromatization catalyst.

* * * * *